US011241495B2

(12) United States Patent
Biemans et al.

(10) Patent No.: US 11,241,495 B2
(45) Date of Patent: Feb. 8, 2022

(54) IMMUNOGENIC COMPOSITION

(71) Applicant: GLAXOSMITHKLINE BIOLOGICALS S.A., Rixensart (BE)

(72) Inventors: Ralph Leon Biemans, Rixensart (BE); Dominique Boutriau, Rixensart (BE); Carine Capiau, Rixensart (BE); Philippe Denoel, Rixensart (BE); Pierre Duvivier, Rixensart (BE); Jan Poolman, Rixensart (BE)

(73) Assignee: Glaxosmithkline Biologicals S.A., Rixensart (BE)

( * ) Notice: Subject to any disclaimer, the term of this patent is extended or adjusted under 35 U.S.C. 154(b) by 0 days.

(21) Appl. No.: 16/179,476

(22) Filed: Nov. 2, 2018

(65) Prior Publication Data
US 2019/0298822 A1 Oct. 3, 2019

Related U.S. Application Data

(63) Continuation of application No. 15/691,440, filed on Aug. 30, 2017, now Pat. No. 10,166,287, which is a continuation of application No. 11/917,610, filed as application No. PCT/EP2006/006188 on Jun. 23, 2006, now Pat. No. 9,789,179.

(30) Foreign Application Priority Data

| Jun. 27, 2005 | (GB) | ................................ 0513069 |
| Jun. 27, 2005 | (GB) | ................................ 0513071 |
| Jul. 28, 2005 | (GB) | ................................ 0515556 |
| Nov. 28, 2005 | (GB) | ................................ 0524204 |
| Dec. 21, 2005 | (GB) | ................................ 0526040 |
| Dec. 21, 2005 | (GB) | ................................ 0526041 |

(51) Int. Cl.
| *A61K 39/00* | (2006.01) |
| *A61K 39/385* | (2006.01) |
| *A61K 39/095* | (2006.01) |
| *C07H 3/00* | (2006.01) |
| *A61K 39/102* | (2006.01) |
| *A61K 39/116* | (2006.01) |
| *A61K 39/05* | (2006.01) |
| *A61K 39/08* | (2006.01) |
| *A61K 39/09* | (2006.01) |
| *A61K 39/02* | (2006.01) |
| *A61K 39/29* | (2006.01) |
| *A61K 39/145* | (2006.01) |
| *C12N 7/00* | (2006.01) |
| *A61K 39/12* | (2006.01) |

(52) U.S. Cl.
CPC ........ *A61K 39/385* (2013.01); *A61K 39/0017* (2013.01); *A61K 39/0018* (2013.01); *A61K 39/05* (2013.01); *A61K 39/08* (2013.01); *A61K 39/092* (2013.01); *A61K 39/095* (2013.01); *A61K 39/099* (2013.01); *A61K 39/102* (2013.01); *A61K 39/116* (2013.01); *A61K 39/145* (2013.01); *A61K 39/292* (2013.01); *C07H 3/00* (2013.01); *C12N 7/00* (2013.01); *A61K 39/12* (2013.01); *A61K 2039/545* (2013.01); *A61K 2039/55* (2013.01); *A61K 2039/575* (2013.01); *A61K 2039/6037* (2013.01); *A61K 2039/62* (2013.01); *A61K 2039/627* (2013.01); *A61K 2039/70* (2013.01); *C12N 2730/10134* (2013.01); *C12N 2760/16234* (2013.01); *C12N 2760/16271* (2013.01); *C12N 2770/32634* (2013.01); *Y02A 50/30* (2018.01)

(58) Field of Classification Search
CPC .................................................... A61K 39/385
See application file for complete search history.

(56) References Cited

U.S. PATENT DOCUMENTS

| 4,057,685 A | 11/1977 | McIntire |
| 4,123,520 A | 10/1978 | Hagopian et al. |
| 4,206,200 A * | 6/1980 | Guthohrlein ......... A61K 9/0019 |
| | | 424/250.1 |
| 4,235,877 A | 11/1980 | Fullerton |
| 4,235,994 A | 11/1980 | Stoudt et al. |
| 4,365,170 A | 12/1982 | Okuhara |
| 4,459,286 A | 7/1984 | Hilleman et al. |
| 4,673,574 A | 6/1987 | Anderson |
| 4,709,017 A | 11/1987 | Collier et al. |
| 4,727,136 A | 2/1988 | Jennings et al. |
| 4,808,700 A | 2/1989 | Anderson et al. |
| 4,950,740 A | 8/1990 | Greenfield et al. |
| 5,651,971 A | 7/1997 | Lees |

(Continued)

FOREIGN PATENT DOCUMENTS

| BR | PI 0508813-5 A | 8/2007 |
| CA | 2004810 A1 | 6/1990 |

(Continued)

OTHER PUBLICATIONS

Arakawa et al (Biochemistry vol. 21, pp. 6536-6544) (Year: 1982).*

(Continued)

*Primary Examiner* — Albert M Navarro

(74) *Attorney, Agent, or Firm* — Seed IP Law Group LLP

(57) ABSTRACT

The present application discloses an immunogenic composition comprising *N. meningitidis* capsular polysaccharides from at least one of serogroups A, C, W135 and Y conjugated to a carrier protein to produce a *N. meningitidis* capsular polysaccharide conjugate, wherein the average size of each *N. meningitidis* polysaccharide is above 50 kDa.

5 Claims, 1 Drawing Sheet

(56) References Cited

U.S. PATENT DOCUMENTS

| | | | |
|---|---|---|---|
| 5,698,677 A * | 12/1997 | Eibl | C12N 9/96 530/381 |
| 5,843,711 A | 12/1998 | Collier et al. | |
| 5,849,301 A | 12/1998 | Lees | |
| 5,869,058 A | 2/1999 | Cohen et al. | |
| 5,917,017 A | 6/1999 | Collier et al. | |
| 5,965,714 A | 10/1999 | Ryall | |
| 6,146,902 A | 11/2000 | McMaster | |
| 6,251,401 B1 | 6/2001 | Ceccarini et al. | |
| 6,455,673 B1 | 9/2002 | Collier | |
| 6,656,472 B1 | 12/2003 | Chong et al. | |
| 6,855,321 B1 | 2/2005 | Rappouli et al. | |
| 6,936,261 B2 | 8/2005 | Granoff et al. | |
| 7,018,637 B2 | 3/2006 | Chong et al. | |
| 7,122,191 B2 | 10/2006 | Dominowski et al. | |
| 7,348,006 B2 | 3/2008 | Contorni et al. | |
| 7,628,995 B2 | 12/2009 | Bos et al. | |
| 7,754,218 B2 | 7/2010 | Contorni et al. | |
| 7,838,014 B2 | 11/2010 | Biemans et al. | |
| 7,867,498 B2 | 1/2011 | Rappouli et al. | |
| 7,939,087 B2 | 5/2011 | Telford et al. | |
| 8,007,807 B2 | 8/2011 | Borkowski | |
| 8,039,007 B2 | 10/2011 | Rappouli et al. | |
| 8,062,641 B2 | 11/2011 | Oscarson et al. | |
| 8,192,746 B2 | 6/2012 | Caulfield et al. | |
| 8,221,770 B2 | 7/2012 | Biemans et al. | |
| 8,309,327 B2 | 11/2012 | Biemans et al. | |
| 8,329,184 B2 | 12/2012 | Biemans et al. | |
| 8,398,983 B2 | 3/2013 | Biemans et al. | |
| 8,409,587 B2 | 4/2013 | Mayeresse et al. | |
| 8,431,136 B2 | 4/2013 | Biemans et al. | |
| 8,574,596 B2 | 11/2013 | Castado et al. | |
| 8,663,656 B2 | 3/2014 | Pizza | |
| 8,679,770 B2 | 3/2014 | De Vleeschauwer et al. | |
| 8,703,148 B2 | 4/2014 | Biemans et al. | |
| 8,753,645 B2 | 6/2014 | Biemans et al. | |
| 8,753,651 B2 | 6/2014 | Costantino | |
| 8,758,764 B2 | 6/2014 | Masignani et al. | |
| 8,802,111 B2 | 8/2014 | Contorni | |
| 8,815,254 B2 | 8/2014 | Biemans et al. | |
| RE45,137 E | 9/2014 | O'Hagan et al. | |
| 8,883,163 B2 | 11/2014 | Biemans et al. | |
| 8,883,166 B2 | 11/2014 | Contorni et al. | |
| 10,166,287 B2 * | 1/2019 | Biemans | A61K 39/145 |
| 2003/0099672 A1 | 5/2003 | Schultz | |
| 2003/0180316 A1 | 9/2003 | Boutriau et al. | |
| 2004/0096461 A1 | 5/2004 | Michon et al. | |
| 2004/0126389 A1 | 7/2004 | Berthet et al. | |
| 2004/0202668 A1 | 10/2004 | Boutriau et al. | |
| 2004/0213804 A1 | 10/2004 | Michon et al. | |
| 2005/0019337 A1 | 1/2005 | Ryall | |
| 2005/0020813 A1 | 1/2005 | Masignani et al. | |
| 2005/0025780 A1 | 2/2005 | Rubido et al. | |
| 2005/0106181 A1 | 5/2005 | Constantino | |
| 2005/0208079 A1 | 9/2005 | Cassone et al. | |
| 2006/0051378 A1 | 3/2006 | Guidice et al. | |
| 2006/0115490 A1 | 6/2006 | Masignani et al. | |
| 2006/0121055 A1 | 6/2006 | Campbell et al. | |
| 2006/0121059 A1 | 6/2006 | Garcon et al. | |
| 2006/0166344 A1 | 7/2006 | Pizza et al. | |
| 2006/0251670 A1 | 11/2006 | Comanducci et al. | |
| 2006/0257413 A1 | 11/2006 | Zlotnick et al. | |
| 2006/0275315 A1 | 12/2006 | Telford et al. | |
| 2008/0199490 A1 | 8/2008 | Biemans et al. | |
| 2008/0241180 A1 | 10/2008 | Contorni | |
| 2008/0248059 A1 | 10/2008 | Capannoli et al. | |
| 2008/0260773 A1 | 10/2008 | Del Giudice et al. | |
| 2008/0305127 A1 | 12/2008 | Poolman | |
| 2009/0010959 A1 | 1/2009 | Biemans et al. | |
| 2009/0017059 A1 | 1/2009 | Biemans et al. | |
| 2009/0017072 A1 | 1/2009 | Biemans et al. | |
| 2009/0041802 A1 | 2/2009 | Biemans et al. | |
| 2009/0043077 A1 | 2/2009 | Berti | |
| 2009/0060945 A1 | 3/2009 | Marshall | |
| 2009/0136541 A1 | 5/2009 | Biemans et al. | |
| 2009/0162394 A1 | 6/2009 | Biemans et al. | |
| 2009/0214586 A1 | 8/2009 | Contorni et al. | |
| 2009/0252759 A1 | 10/2009 | Biemans et al. | |
| 2009/0311285 A1 | 12/2009 | Biemans et al. | |
| 2010/0074918 A1 | 3/2010 | Poolman | |
| 2010/0104593 A1 | 4/2010 | Marshall | |
| 2010/0143399 A1 | 6/2010 | Biemans et al. | |
| 2010/0183662 A1 | 7/2010 | Biemans et al. | |
| 2010/0203137 A1 | 8/2010 | Contorni et al. | |
| 2010/0209450 A1 | 8/2010 | Biemans et al. | |
| 2010/0215686 A1 | 8/2010 | Biemans et al. | |
| 2013/0122040 A1 | 5/2013 | Blackkolb et al. | |
| 2013/0216571 A1 | 8/2013 | Ryall | |

FOREIGN PATENT DOCUMENTS

| | | |
|---|---|---|
| CN | 1401328 A | 3/2003 |
| CN | 1425465 A | 6/2003 |
| CN | 1709505 A | 12/2005 |
| EP | 0 211 258 A2 | 2/1987 |
| EP | 0 161 188 B1 | 4/1991 |
| EP | 0 208 375 B1 | 12/1991 |
| EP | 0 378 881 B1 | 6/1993 |
| EP | 0 477 508 B1 | 7/1995 |
| EP | 0 427 347 B1 | 2/1996 |
| EP | 0 471 177 B1 | 10/1996 |
| EP | 0 497 524 B1 | 7/1998 |
| EP | 0 497 525 B1 | 8/1998 |
| EP | 0 594 610 B1 | 9/1998 |
| EP | 0 594 950 B1 | 1/1999 |
| EP | 0 941 738 B1 | 5/2005 |
| EP | 1 946 769 B1 | 5/2012 |
| WO | 91/01146 A1 | 2/1991 |
| WO | 91/08772 A1 | 6/1991 |
| WO | 93/17712 A1 | 6/1993 |
| WO | 93/15760 A1 | 8/1993 |
| WO | 93/24148 A1 | 12/1993 |
| WO | 94/03208 A1 | 2/1994 |
| WO | 95/08348 A1 | 3/1995 |
| WO | 94/14086 A1 | 5/1996 |
| WO | 96/29094 A1 | 9/1996 |
| WO | 96/40242 A1 | 12/1996 |
| WO | 97/00697 A1 | 1/1997 |
| WO | 97/35613 A1 | 10/1997 |
| WO | 99/18121 A1 | 9/1998 |
| WO | 98/42721 A1 | 10/1998 |
| WO | 98/51339 A1 | 11/1998 |
| WO | 98/58668 A2 | 12/1998 |
| WO | 99/13906 A1 | 3/1999 |
| WO | 99/55715 A2 | 4/1999 |
| WO | 99/42130 A1 | 8/1999 |
| WO | 99/48525 A1 | 9/1999 |
| WO | 00/10599 A2 | 3/2000 |
| WO | 00/50006 A2 | 8/2000 |
| WO | 00/56360 A2 | 9/2000 |
| WO | 00/61761 A2 | 10/2000 |
| WO | 01/00790 A1 | 1/2001 |
| WO | 01/30390 A2 | 5/2001 |
| WO | 01/41800 A2 | 6/2001 |
| WO | 01/72337 A1 | 10/2001 |
| WO | 02/00249 A2 | 1/2002 |
| WO | 02/058737 A2 | 8/2002 |
| WO | 02/080965 A2 | 10/2002 |
| WO | 02/091998 A2 | 11/2002 |
| WO | 03/007985 A2 | 1/2003 |
| WO | 03/078453 A1 | 9/2003 |
| WO | 03/080678 A1 | 10/2003 |
| WO | 03/094834 A2 | 11/2003 |
| WO | 03/094960 A2 | 11/2003 |
| WO | 2004/011027 A1 | 2/2004 |
| WO | 2004/020463 A2 | 3/2004 |
| WO | 2004/032958 A1 | 4/2004 |
| WO | 2004/048404 A2 | 6/2004 |
| WO | 2004/067030 A2 | 8/2004 |
| WO | 2004/067033 A1 | 8/2004 |
| WO | 2004/083251 A2 | 9/2004 |
| WO | 2004/103400 A2 | 12/2004 |
| WO | 2004/110480 A2 | 12/2004 |
| WO | 2005/000345 A2 | 1/2005 |

(56) References Cited

FOREIGN PATENT DOCUMENTS

| WO | 2005/020964 A1 | 3/2005 |
|---|---|---|
| WO | 2005/032583 A2 | 4/2005 |
| WO | 2005/089794 A2 | 9/2005 |
| WO | 2005/105140 A2 | 11/2005 |
| WO | 2006/075170 A1 | 7/2006 |
| WO | 2006/097851 A2 | 9/2006 |
| WO | 2007/000322 A1 | 1/2007 |
| WO | 2007/000327 A1 | 1/2007 |
| WO | 2007/000341 A2 | 1/2007 |
| WO | 2007/000342 A2 | 1/2007 |
| WO | 2007/000343 A2 | 1/2007 |
| WO | 2008/011201 A2 | 1/2008 |
| WO | 2008/081014 A2 | 7/2008 |
| WO | 2008/081022 A1 | 7/2008 |
| WO | 2008/135514 A1 | 11/2008 |
| WO | 2008/149238 A2 | 12/2008 |
| WO | 2009/016515 A2 | 2/2009 |

OTHER PUBLICATIONS

Agbarakwe et al., "Avidity of specific IgG antibodies elicited by immunisation against *Haemophilus influenzae* type b," *Journal of Clinical Pathology* 48(3):206-209, 1995. (5 pages).

Amir et al., "Immunogenicity and safety of a liquid combination of DT-PRP-T vs lyophilized PRP-T reconstituted with DTP," *Vaccine* 15(2):149-154, 1997.

Anderson et al., "Safety and Immunogenicity of Meningococcal A and C Polysaccharide Conjugate Vaccine in Adults," *Infection and Immunity* 62(8):3391-3395, 1994.

Anderson et al., "Safety, tolerability and immunogenicity of low dose *Haemophilus influenzae* type b conjugated to the outer membrane protein complex of *Neisseria meningitidis* group B," *The Pediatric Infectious Disease Journal* 21(4):350-352, 2002.

André, "Development and clinical application of new polyvalent combined paediatric vaccines," *Vaccine* 17(13-14):1620-1627, 1999.

Arístegui et al., "Comparison of the reactogenicity and immunogenicity of a combined diphtheria, tetanus, acellular pertussis, hepatitis B, inactivated polio (DTPa-HBV-IPV) vaccine, mixed with the *Haemophilus influenzae* type b (Hib) conjugate vaccine and administered as a single injection, with the DTPa-IPV/Hib and hepatitis B vaccines administered in two simultaneous injections to infants at 2, 4, and 6 months of age," *Vaccine* 21(25-26):3593-3600, 2003.

Avendano et al., "*Haemophilus influenzae* type b polysaccharide-tetanus protein conjugate vaccine does not depress serologic responses to diphtheria, tetanus or pertussis antigens when coadministered in the same syringe with diphtheria-tetanus-pertussis vaccine at two, four and six months of age," *The Pediatric Infectious Disease Journal* 12(8):638-643, 1993.

Baraldo et al., "N19 Polyepitope as a Carrier for Enhanced Immunogenicity and Protective Efficacy of Meningococcal Conjugate Vaccines," *Infection and Immunity* 72(8):4884-4887, 2004.

Bardotti et al., "Physicochemical characterisation of glycoconjugate vaccines for prevention of meningococcal diseases," *Vaccine* 26(18):2284-2296, 2008.

Barington et al., "Non-Epitope-Specific Suppression of the Antibody Response to *Haemophilus influenzae* Type b Conjugate Vaccines by Preimmunization with Vaccine Components.," *Infection and Immunity* 61(2):432-438, 1993. (8 pages).

Barington et al., "Opposite Effects of Actively and Passively Acquired Immunity to the Carrier on Responses of Human Infants to a *Haemophilus influenzae* Type b Conjugate Vaccine," *Infection and Immunity* 62(1):9-14, 1994. (7 pages).

Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guérin priming," *European Journal of Immunology* 22(6):1365-1372, 1992.

Berry et al., "Effect of O Acetylation of *Neisseria meningitidis* Serogroup A Capsular Polysaccharide on Development of Functional Immune Responses," *Infection and Immunity* 70(7):3707-3713, 2002. (8 pages).

Bethell et al., "A Novel Method of Activation of Cross-linked Agaroses with 1,1'-Carbonyldiimidazole Which Gives a Matrix for Affinity Chromatography Devoid of Additional Charged Groups," *The Journal of Biological Chemistry* 254(8):2572-2574, 1979.

Borrow et al., "Long-term protection in children with meningococcal C conjugate vaccination: lessons learned," *Expert Review of Vaccines* 5(6):851-857, 2006.

Bravo et al., "The new DTPw-HBV-Hib combination vaccine can be used at the WHO schedule with a monovalent dose of hepatitis B vaccine at birth," *The Southeast Asian Journal of Tropical Medicine and Public Health* 29(4):772-778, 1998.

Burrage et al., "Effect of Vaccination with Carrier Protein on Response to Meningococcal C Conjugate Vaccines and Value of Different Immunoassays as Predictors of Protection," *Infection and Immunity* 70(9):4946-4954, 2002. (10 pages).

Buttery et al., "Immunogenicity and Safety of a Combination Pneumococcal-Meningococcal Vaccine in Infants," *The Journal of the American Medical Association* 293(14):1751-1758, 2005.

Cai et al., "LC/MS Characterization of Meningococcal Depolymerized Polysaccharide Group C Reducing Endgroup and Internal Repeating Unit," *Analytical Chemistry* 76(24):7387-7390, 2004.

Campbell et al., "Safety, Reactogenicity, and Immunogenicity of a Tetravalent Meningococcal Polysaccharide-Diphtheria Toxoid Conjugate Vaccine Given to Healthy Adults," *The Journal of Infectious Diseases* 186(12):1848-1851, 2002.

Campbell et al., "Standard and alternative regimens of *Haemophilus influenzae* type b conjugate vaccine (polyribosylribitol phosphate-tetanus toxoid conjugate vaccine) elicit comparable antibody avidities in infants," *The Pediatric Infectious Disease Journal* 21(9):822-826, 2002.

Chippaux et al., "Immunogenicity, safety, and memory of different schedules of *Neisseria meningitidis* A/C-diphtheria toxoid conjugate vaccine in infants in Niger," *Vaccine* 22(25-26):3303-3311, 2004.

Choo et al., "Immunogenicity and reactogenicity of a group C meningococcal conjugate vaccine compared with a group A+C meningococcal polysaccharide vaccine in adolescents in a randomised observer-blind controlled trial," *Vaccine* 18(24):2686-2692, 2000.

Choo et al., "Immunogenicity and reactogenicity of a pneumococcal conjugate vaccine administered combined with a *Haemophilus influenzae* type b conjugate vaccine in United Kingdom infants," *The Pediatric Infectious Disease Journal* 19(9):854-862, 2000.

Chu et al., "Further Studies on the Immunogenicity of *Haemophilus influenzae* Type b and Pneumococcal Type 6A Polysaccharide-Protein Conjugates," *Infection and Immunity* 40(1):245-256, 1983.

Claesson et al., "Clinical and immunologic responses to the capsular polysaccharide of *Haemophilus influenzae* type b alone or conjugated to tetanus toxoid in 18- to 23-month-old children," *The Journal of Pediatrics* 112(5):695-702, 1988.

Conterno et al., "Conjugate vaccines for preventing meningococcal C meningitis and septicaemia..," *Cochrane Database of Systematic Reviews*, vol. 3:CD001834, 2006. (Abstract Only).

Corbel, "Control Testing of Combined Vaccines: A Consideration of Potential Problems and Approaches," *Biologicals* 22(4):353-360, 1994.

Costantino et al., "Development and phase 1 clinical testing of a conjugate vaccine against meningococcus A and C," *Vaccine* 10(10):691-698, 1992.

Dagan et al., "Glycoconjugate vaccines and immune interference: A review," *Vaccine* 28(34):5513-5523, 2010.

Dagan et al., "Reduced Response to Multiple Vaccines Sharing Common Protein Epitopes That Are Administered Simultaneously to Infants," *Infection and Immunity* 66(5):2093-2098, 1998.

De Bolle et al., "The length of a tetranucleotide repeat tract in *Haemophilus influenzae* determines the phase variation rate of a gene with homology to type III DNA methyltransferases," *Molecular Microbiology* 35(1):211-222, 2000.

Drachenberg et al., "A well-tolerated grass pollen-specific allergy vaccine containing a novel adjuvant, monophosphoryl lipid A, reduces allergic symptoms after only four preseasonal injections," *Allergy* 56(6):498-505, 2001.

European Centre for Disease Prevention and Control, *Haemophilus influenzae* type b (Hib), Factsheet for health professionals, URL=

(56) References Cited

OTHER PUBLICATIONS http://www.ecdc.europa.eu/en/healthtopics/Haemophilus_Influenzae_Infection/basic_facts/Pages/healthprofessionals.aspx, download date Apr. 22, 2013, 3 pages.

European Medicines Agency, Announcement of Grant of Marketing Authorisation for the Prevenar Pneumococcal Conjugate Vaccine, Committee for Proprietary Medicinal Products European Public Assessment Report, 2001.

European Medicines Agency, Guideline on Adjuvants in Vaccines for Human Use, Committee for Medicinal Products for Human Use, 2005. (18 pages).

European Medicines Agency, Infanrix Hexa: EPAR—Product Information, published Nov. 26, 2008. (First Page).

Falugi et al., "Rationally designed strings of promiscuous CD4+ T cell epitopes provide help to *Haemophilus influenzae* type b oligosaccharide: a model for new conjugate vaccines," *The European Journal of Immunology* 31(12):3816-3824, 2001.

Fattom et al., "Epitopic overload at the site of injection may result in suppression of the immune response to combined capsular polysaccharide conjugate vaccines," *Vaccine* 17(2):126-133, 1999.

Fernández et al., "Randomized trial of the immunogenicity of fractional dose regimens of PRP-T *Haemophilus influenzae* type b conjugate vaccine," *The American Journal of Tropical Medicine and Hygiene* 62(4):485-490, 2000.

Foster et al., "New therapies and vaccines for bacterial meningitis," *Expert Opinion on Investigational Drugs* 11(8): 1051-1060, 2002.

Frasch, "Preparation of bacterial polysaccharide-protein conjugates: Analytical and manufacturing challenges," *Vaccine* 27(46):6468-6470, 2009.

Gatchalian et al., "Antibody persistence and immune memory in 10-month-old infants primed with Tritanrix™-HepB/Hib-MenAC at 6, 10, 14 weeks of age," *14th International Pathogenic Neisseria Conference*, Milwaukee, WI, USA, Sep. 5-10, 2004, 2 pages. (Abstract and Poster only).

Gatchalian et al., "Immunogenicity and safety of 3 doses of Tritanrix™-HepB/Hib-MenAC vaccine administered to infants at 6, 10, and 14 weeks of age," *14th International Pathogenic Neisseria Conference*, Milwaukee, WI, USA, Sep. 5-10, 2004, 2 pages. (Abstract and Poster only).

Gatchalian et al., "The development of a new heptavalent diphtheria-tetanus-whole cell pertussis-hepatitis B-*Haemophilus influenzae* type b-*Neisseria meningitidis* serogroups A and C vaccine: a randomized dose-ranging trial of the conjugate vaccine components," *International Journal of Infectious Diseases* 12(3):278-288, 2008.

Geyer et al., "Immunochemical Properties of Oligosaccharide-Protein Conjugates with *Klebsiella*-K2 Specificity," *Medical Microbiology and Immunology* 165(4):271-288, 1979.

Girard et al., "A review of vaccine research and development: Meningococcal disease," *Vaccine* 24(22):4692-4700, 2006.

GlaxoSmithKline, Hiberix® Consumer Medicine Information, May 16, 2011, 3 pages.

Granoff, "Meningococcal polysaccharide-protein conjugate vaccines," *Conjugate and Polysaccharide Vaccines*, Plenary Review, (39 pages) Retrieved from the Internet: URL:http://neisseria.org/ipnc/1996/Neis1996-chap4 (Jan. 1, 1996).

Granoff et al., "Meningococcal Polysaccharide-Protein Conjugate Vaccines," *International Journal of Infectious Diseases* 1(3):152-157, 1997.

Granoff et al., "MF59 Adjuvant Enhances Antibody Responses of Infant Baboons Immunized with *Haemophilus influenzae* Type b and *Neisseria meningitidis* Group C Oligosaccharide-CRM$_{197}$ Conjugate Vaccine," *Infection and Immunity* 65(5):1710-1715, 1997.

Granoff et al., Chapter 34, "Meningococcal Vaccines," in Plotkin & Mortimer (ed.), *Vaccines, 4th* ed., W. B. Saunders Co., Philadelphia, 2004, pp. 959-987.

Gupta et al., "Biodegradable Polymer Microspheres as Vaccine Adjuvants and Delivery Systems," *Developments in Biological Standardization* 92:63-78, Proceedings of Modulation of the Immune Response to Vaccine Antigens: Symposium, Bergen, Norway, Jun. 18-21, 1996.

Hearn et al., "Application of 1,1'-carbonyldiimidazole-activated matrices for the purification of proteins: III. The use of 1,1'-carbonyldiimidazole-activated agaroses in the biospecific affinity chromatographic isolation of serum antibodies," *Journal of Chromatography* 218:509-518, 1981.

Huebner et al., "Dose response of CRM$_{197}$ and tetanus toxoid-conjugated *Haemophilus influenzae* type b vaccines," *Vaccine* 23(6):802-806, 2004.

Jennings et al., "Immunochemistry of groups A, B, and C meningococcal polysaccharide-tetanus toxoid conjugates," *The Journal of Immunology* 127(3):1011-1018, 1981.

Joshi et al., "Meningococcal polysaccharide vaccines: A review," *Carbohydrate Polymers* 75(4):553-565, 2009.

Kuo et al., "Characterization of a Recombinant Pneumolysin and Its Use as a Protein Carrier for Pneumococcal Type 18C Conjugate Vaccines," *Infection and Immunity* 63(7):2706-2713, 1995.

Lagos et al., "Economisation of vaccination against *Haemophilus influenzae* type b: a randomised trial of immunogenicity of fractional-dose and two-dose regimens," *The Lancet* 351(9114):1472-1476, 1998.

Lakshman et al., "Meningococcal serogroup C conjugate vaccine," *Expert Opinion on Biological Therapy* 2(1):87-96, 2002.

Lepow, Chapter 17, "Meningococcal Vaccines," in Plotkin & Mortimer (ed.), *Vaccines, 2nd* ed., W. B. Saunders Co., Philadelphia, 1994, pp. 503-515. (16 pages).

Lowry et al., "Protein measurement with the folin phenol reagent," *The Journal of Biological Chemistry* 193(1):265-275, 1951.

MacLennan et al., "Safety, Immunogenicity, and Induction of Immunologic Memory by a Serogroup C Meningococcal Conjugate Vaccine in Infants: A Randomized Controlled Trial," *The Journal of the American Medical Association* 283(21):2795-2801, 2000.

Mendelman et al., "Immunogenicity and safety of *Haemophilus influenzae* type b polysaccharide-*Neisseria meningitidis* conjugate vaccine in 7.5 µg liquid formulation: a comparison of three lots with the 15.0 µg lyophilized formulation," *Vaccine* 15(6-7):775-781, 1997.

Molrine et al., "Antibody Responses to Polysaccharide and Polysaccharide-Conjugate Vaccines after Treatment of Hodgkin Disease," *Annals of Internal Medicine* 123(11):828-834, 1995.

Monsigny et al., "Colorimetric Determination of Neutral Sugars by a Resorcinol Sulfuric Acid Micromethod," *Analytical Biochemistry* 175(2):525-530, 1988.

Nicol et al., "*Haemophilus influenzae* type b conjugate vaccine diluted tenfold in diphtheria-tetanus-whole cell pertussis vaccine: a randomized trial," *The Pediatric Infectious Disease Journal* 21(2):138-141, 2002. (8 pages).

Nolan et al., "A novel combined *Haemophilus influenzae* type b-*Neisseria meningitidis* serogroups C and Y-tetanus-toxoid conjugate vaccine is immunogenic and induces immune memory when co-administered with DTPa-HBV-IPV and conjugate pneumococcal vaccines in infants," *Vaccine* 25(51):8487-8499, 2007.

Obaro et al., "Safety and immunogenicity of pneumococcal conjugate vaccine in combination with diphtheria, tetanus toxoid, pertussis and *Haemophilus influenzae* type b conjugate vaccine," *The Pediatric Infectious Disease Journal* 21(10):940-946, 2002. (8 pages).

Papaevangelou, "Current combined vaccines with hepatitis B," *Vaccine* 16(Supplement 1):S69-S72, 1998.

Paradiso et al., "Glycoconjugate Vaccines: Future Combinations," *Developments in Biological Standardization* 87:269-275, Proceedings of New Approaches to Stabilisation of Vaccines Potency, Geneva, Switzerland, May 29-31, 1995. (4 pages).

Paradiso et al., "Introduction to Combination Vaccines," Abstract S15, *1st Annual Conference on Vaccine Research*, Washington D.C., USA, May 30-Jun. 1, 1998.

Pasteur Mérieux Connaught, "Haemophilus b Conjugate Vaccine (Tetanus Toxoid Conjugate) ActHIB®," Product Information, A.H.F.S. Category 80:12, 1996.

Pato et al., "Purification of capsular polysaccharide from *Neisseria meningitidis* serogroup C by liquid chromatography," *J Chromatogr B Analyt Technol Biomed Life Sci* 832(2):262-267, 2006.

(56) References Cited

OTHER PUBLICATIONS

Peeters et al., "Effect of Carrier Priming on Immunogenicity of Saccharide-Protein Conjugate Vaccines," *Infection and Immunity* 59(10):3504-3510, 1991. (8 pages).

Perkins, "New Opportunities for Prevention of Meningococcal Disease," *The Journal of the American Medical Association* 283(21):2842-2843, 2000. (3 pages).

Peterson, "Review of the Folin Phenol Protein Quantitation Method of Lowry, Rosebrough, Farr and Randall," *Analytical Biochemistry* 100(2):201-220, 1979.

Pines et al., "New acellular pertussis-containing paediatric combined vaccines," *Vaccine* 17(13-14):1650-1656, 1999. (8 pages)

Plotkin et al. (ed.), *Vaccines,* $3^{rd}$ ed., W. B. Saunders Co., Philadelphia, 1999, pp. 200-202. (5 pages).

Poland, "The burden of pneumococcal disease: the role of conjugate vaccines," *Vaccine* 17(13-14):1674-1679, 1999.

Pöllabauer et al., "The influence of carrier protein on the immunogenicity of simultaneously administered conjugate vaccines in infants," *Vaccine* 27(11):1674-1679, 2009.

Rappuoli et al., "New vaccines, especially new combined vaccines," Report of the Expert Panel VIII, European Commission Cost/STD Initiative, *Vaccine* 14(7):691-700, 1996.

Rappuoli, "Conjugates and reverse vaccinology to eliminate bacterial meningitis," *Vaccine* 19(17-19):2319-2322, 2001.

Rennels et al., "Dose escalation, safety and immunogenicity study of a tetravalent meningococcal polysaccharide diphtheria conjugate vaccine in toddlers," *The Pediatric Infectious Disease Journal* 21(10):978-979, 2002.

Rennels et al., "Safety and Immunogenicity of Combined Conjugate 9-Valent *S. pneumoniae*-meningococcal group C (9vPnC-MnCC) and *H. influenza* b-9vPnC-MnCC (HbOC-9vPnC-MnCC) Vaccine," Abstract G-2039, $41^{st}$ *Interscience Conference of Antimicrobial Agents and Chemotherapy,* Chicago, IL, USA, Dec. 16-19, 2001, 1 page.

Rennels et al., "Safety and Immunogenicity of Heptavalent Pneumococcal Vaccine Conjugated to $CRM_{197}$ in United States Infants," *Pediatrics* 101(4):604-611, 1998. (10 pages).

Richmond et al., "Evaluation of De-O-Acetylated Meningococcal C Polysaccharide-Tetanus Toxoid Conjugate Vaccine in Infancy: Reactogenicity, Immunogenicity, Immunologic Priming, and Bactericidal Activity against O-Acetylated and De-O-Acetylated Serogroup C Strains," *Infection and Immunity* 69(4):2378-2382, 2001.

Richmond et al., "Meningococcal Serogroup C Conjugate Vaccine is Immunogenic in Infancy and Primes for Memory," *The Journal of Infectious Diseases* 179(6):1569-1572, 1999.

Richmond et al., "Safety and immunogenicity of a new *Neisseria meningitidis* serogroup C-tetanus toxoid conjugate vaccine in healthy adults," *Vaccine* 18(7-8):641-646, 2000.

Romero-Steiner et al., "Functional Antibody Activity Elicited by Fractional Doses of *Haemophilus influenzae* Type b Conjugate Vaccine (Polyribosylribitol Phosphate-Tetanus Toxoid Conjugate)," *Clinical and Diagnostic Laboratory Immunology* 8(6):1115-1119, 2001.

Schneerson et al., "Quantitative and Qualitative Analyses of Serum Antibodies Elicited in Adults by *Haemophilus influenzae* Type b and Pneumococcus Type 6A Capsular Polysaccharide-Tetanus Toxoid Conjugates," *Infection and Immunity* 52(2):519-528, 1986. (11 pages).

Siber et al., "Development of a guinea pig model to assess immunogenicity of *Haemophilus influenzae* type b capsular polysaccharide conjugate vaccines," *Vaccine* 13(6):525-531, 1995.

Silveira et al., "Characterization and immunogenicity of meningococcal group C conjugate vaccine prepared using hydrazide-activated tetanus toxoid," *Vaccine* 25(41):7261-7270, 2007.

Snape et al., "Meningococcal polysaccharide-protein conjugate vaccines," *The Lancet Infectious Diseases* 5(1):21-30, 2005.

Sood et al., "Capsular polysaccharide-protein conjugate vaccines," *Drug Discovery Today* 1(9):381-387, 1996.

Takahashi et al., "Induction of $CD8^+$ cytotoxic T cells by immunization with purified HIV-1 envelope protein in ISCOMs," *Nature* 344(6269):873-875, 1990.

Tamm et al., "Double-blind study comparing the immunogenicity of a licensed DTwPHib-CRM197 conjugate vaccine (Quattvaxem$^{TM}$) with three investigational, liquid formulations using lower doses of Hib-CRM197 conjugate," *Vaccine* 23(14):1715-1719, 2005.

Tan, "Pneumococcal conjugate vaccines—implications for community antibiotic prescribing," *Current Opinion in Microbiology* 3(5):502-507, 2000.

Uchida et al., "Diphtheria Toxin and Related Proteins," *The Journal of Biological Chemistry* 248(11):3838-3844, 1973.

Ugozzoli et al., "Combinations of Protein Polysaccharide Conjugate Vaccines for Intranasal Immunization," *The Journal of Infectious Diseases* 186(9):1358-1361, 2002.

Van der Meeren et al., "Phospholipid composition of r-DNA hepatitis B surface antigens," *International Journal of Pharmaceutics* 106(1):89-92, 1994.

Vanlandschoot et al., "*Saccharomyces cerevisiae*-Derived HBsAg Preparations Differ in Their Attachment to Monocytes, Immune-Suppressive Potential, and T-Cell Immunogenicity," *Journal of Medical Virology* 70(4):513-519, 2003.

von Hunolstein et al., "Synthetic oligodeoxynucleotide containing CpG motif induces an anti-polysaccharide type 1-like immune response after immunization of mice with *Haemophilus influenzae* type b conjugate vaccine," *International Immunology* 12(3):295-303, 2000. (10 pages).

Ward et al., Chapter 12, "*Haemophilus influenzae* vaccines," in Plotkin & Mortimer (ed.), *Vaccines,* $2^{nd}$ ed., W. B. Saunders Co., Philadelphia, 1994, pp. 337-386. (53 pages).

Watemberg et al., "Safety and immunogenicity of *Haemophilus* type b-tetanus protein conjugate vaccine, mixed in the same syringe with diphtheria-tetanus-pertussis vaccine in young infants," *The Pediatric Infectious Disease Journal* 10(10):758-763, 1991.

Wyeth (N.Z.) Limited, Tetramune®, Approved Data Sheet, URL= http://www.ias.org.nz/tetramune.htm, download date Apr. 12, 2003, 10 pages.

Wyeth Lederle Vaccines S.A., Scientific Discussion, Marketing Authorization Application for the Prevenar Pneumococcal Conjugate Vaccine, 2000, 34 pages.

Zangwill et al., "Safety and immunogenicity of a heptavalent pneumococcal conjugate vaccine in infants," *Vaccine* 21(17-18):1894-1900, 2003. (8 pages).

Zepp et al., "Evidence for induction of polysaccharide specific B-cell-memory in the 1st year of life: plain *Haemophilus influenzae* type b—PRP (Hib) boosters children primed with a tetanus-conjugate Hib-DTPa-HBV combined vaccine," *European Journal of Pediatrics* 156(1):18-24, 1997.

Zimmer et al., "Meningococcal conjugate vaccines," *Expert Opinion on Pharmacotherapy* 5(4):855-863, 2004.

Carmenate et al., "Effect of conjugation methodology on the immunogenicity and protective efficacy of meningococcal group C polysaccharide-P64k protein conjugates," *FEMS Immunology and Medical Microbiology* 40:93-\99, 2004.

Michon et al., "Multivalent pneumococcal capsular polysaccharide conjugate vaccines employing genetically detoxified pneumolysin as a carrier protein," *Vaccine* 16(18): 1732-1741, 1998.

\* cited by examiner

FIG. 1A
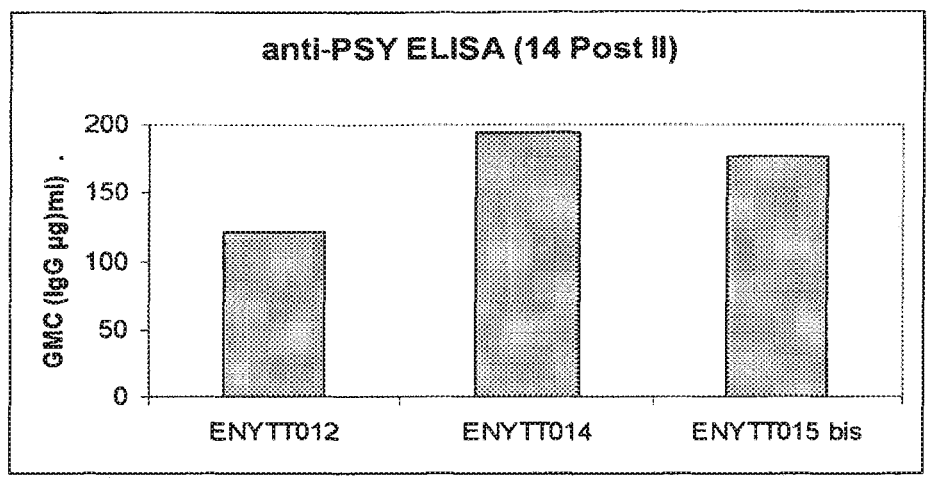
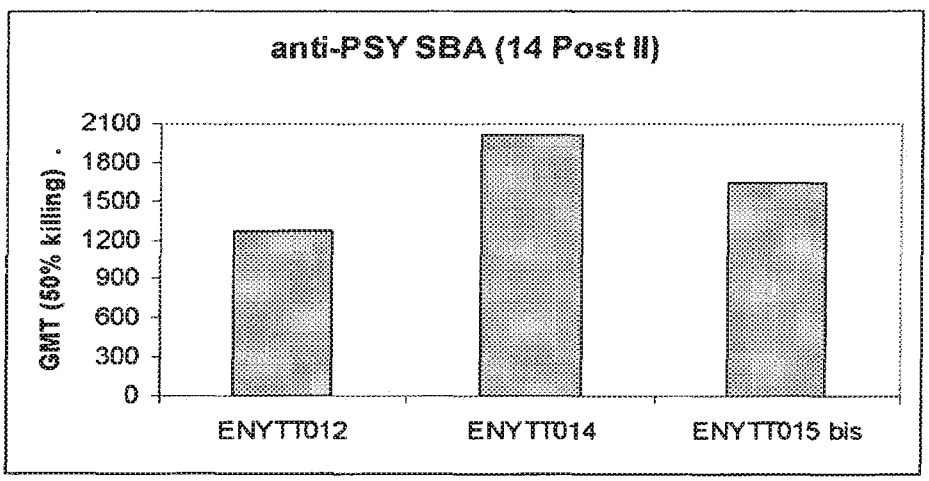
FIG. 1B

IMMUNOGENIC COMPOSITION

The present invention relates to immunogenic compositions comprising *N. meningitidis* capsular polysaccharides conjugated to a carrier protein. It additionally relates to vaccines and vaccine kits comprising *N. meningitidis* polysaccharide conjugates, processes for making the immunogenic compositions and vaccines and the use of the vaccines and immunogenic compositions of the invention in therapy. It also relates to methods of immunising against Neisserial infection using the *N. meningitidis* polysaccharide conjugates and the use of *N. meningitidis* polysaccharide conjugates in the manufacture of a medicament.

*Neisseria meningitidis* is a Gram-negative human pathogen which causes bacterial meningitis. Based on the organism's capsular polysaccharide, twelve serogroups of *N. meningitidis* have been identified (A, B, C, H, I, K, L, 29E, W135, X, Y and Z). Serogroup A (MenA) is the most common cause of epidemic disease in sub-Saharan Africa. Serogroups B and C are responsible for the majority of cases in developing countries, with the remaining cases being caused by W135 and Y).

Immunogenic compositions comprising *N. meningitidis* saccharides conjugated to carrier proteins are known in the art. For instance WO 02/58737 discloses a vaccine comprising purified capsular polysaccharides from *N. meningitidis* serogroups A, C, W135 and Y conjugated to a carrier protein. However, this application teaches that the extracted *N. meningitidis* capsular polysaccharides should be depolymerised by heating in a hydrogen peroxide solution before conjugation.

WO 03/07985 discloses conjugate vaccines comprising *N. meningitidis* saccharide selected from serogroups A, C, W135 and Y. The meningococcal capsular polysaccharides are extracted and then hydrolysed so that a selection of oligosaccharides derived from the capsular polysaccharides are used for conjugation to a carrier protein.

WO 04/103400 also discloses multivalent meningococcal derived polysaccharide-protein conjugate containing capsular polysaccharides derived from *N. meningitidis* serogroups A, C, W135 and Y. This application teaches that, instead of using the large native capsular polysaccharide, the use of meningococcal polysaccharides of a smaller size is preferred. It suggests that capsular polysaccharides are partially depolymerised using mild oxidative conditions to give an average size of less than 100,000 daltons, preferably 12,000 to 25,000 daltons.

There remains a need to develop improved conjugate vaccines against neisserial meningitis. The present invention concerns the provision of a meningococcal polysaccharide conjugate vaccine in which the size of the polysaccharides is larger than that taught in the literature. The focus of the art has been to use oligosaccharides for ease of conjugate production. The inventors has found that by using native or slightly sized polysaccharide conjugates, one or more of the following advantages may be realised: 1) a conjugate having high immungenicity which is filterable; 2) immune memory may be enhanced (as in example three); 3) the alteration of the ratio of polysaccharide to protein in the conjugate such that the ratio of polysaccharide to protein (w/w) in the conjugate may be increased (this can result in a reduction of the carrier suppression effect); 4) immunogenic conjugates prone to hydrolysis (such as MenA conjugates) may be stabilised by the use of larger polysaccharides for conjugation. The use of larger polysaccharides can result in more cross-linking with the conjugate carrier and therefore less cleavage of free saccharide from the conjugate. The conjugate vaccines described in the prior art tend to depolymerise the polysaccharides prior to conjugation in order to improve conjugation. The present invention is directed to a different strategy and surprisingly shows that meningococcal conjugate vaccines retaining a larger size of polysaccharide provide a good immune response against meningococcal disease.

Accordingly, in one aspect of the present invention there is provided an immunogenic composition comprising *N. meningitidis* capsular polysaccharides from at least one, two, three or four of serogroups A, C, W and Y conjugated to a carrier protein, wherein the mean size of each *N. meningitidis* polysaccharide is above 50 kDa, 75 kDa, 100 kDa, 110 kDa, 120 kDa or 130 kDa.

According to a further aspect or the invention there is provided a vaccine comprising the immunogenic composition of the invention and a pharmaceutically acceptable carrier.

According to a further aspect or the invention there is provided a vaccine kit for concomitant or sequential administration comprising two multi-valent immunogenic compositions for conferring protection in a host against disease caused by *Bordetella pertussis, Clostridium tetani, Corynebacterium diphtherias, Haemophilus influenzae* and *Neisseria meningitidis*, said kit comprising a first container comprising:
 tetanus toxoid (TT),
 diphtheria toxoid (DT), and
 whole cell or acellular pertussis components
and a second container comprising:
 *N. meningitidis* capsular polysaccharides from at least one, two, three or four of serogroups A, C, W and Y conjugated to a carrier protein, wherein the average size of the or each *N. meningitidis* polysaccharide is above 50 kDa, 75 kDa, 100 kDa, 110 kDa, 120 kDa or 130 kDa.

According to a further aspect of the invention there is provided a process for making the immunogenic composition or vaccine of the invention comprising the step of mixing *N. meningitidis* capsular polysaccharides from at least one, two, three or four of serogroups A, C, W and Y conjugated to a carrier protein, optionally with a pharmaceutically acceptable excipient, wherein the average size of the or each *N. meningitidis* polysaccharide is above 50 kDa, 75 kDa, 100 kDa, 110 kDa, 120 kDa or 130 kDa.

According to a further aspect or the invention there is provided a method of immunising a human host against disease caused by *Neisseria meningitidis* comprising administering to the host an immunoprotective dose of the immunogenic composition or vaccine of the invention.

According to a further aspect or the invention there is provided an immunogenic composition of the invention for use in the treatment or prevention of disease caused by *Neisseria meningitidis*.

According to a further aspect or the invention there is provided a use of the immunogenic composition or vaccine of the invention in the manufacture of a medicament for the treatment or prevention of diseases caused by *Neisseria meningitidis*.

DESCRIPTION OF FIGURES

FIG. 1A Bar chart showing GMC responses in an anti-MenY ELISA. ENYTT012 is a MenY-TT conjugate prepared from native MenY polysaccharide. ENYTT014 is a MenY-TT conjugate prepared from microfluidised MenY polysaccharide which had undergone 40 cycles of microfluidisation. ENYTT015bis is a MenY-TT conjugate prepared from microfluidised MenY polysaccharide which had undergone 20 cycles of microfluidisation.

FIG. 1B Bar chart showing GMT responses in an anti-MenY SBA assay. ENYTT012 is a MenY-TT conjugate prepared from native MenY polysaccharide. ENYTT014 is a MenY-TT conjugate prepared from microfluidised MenY polysaccharide which had undergone 40 cycles of microfluidisation. ENYTT015bis is a MenY-TT conjugate prepared from microfluidised MenY polysaccharide which had undergone 20 cycles of microfluidisation.

DETAILED DESCRIPTION

An immunogenic composition of the invention comprises *N. meningitidis* capsular polysaccharides from at least one, two, three or four of serogroups A, C, W and Y conjugated to a carrier protein, wherein the average size (weight-average molecular weight; Mw) of at least one, two, three or four or each *N. meningitidis* polysaccharide is above 50 kDa, 60 kDa, 75 kDa, 100 kDa, 110 kDa, 120 kDa or 130 kDa.

In an independent aspect of the invention, the immunogenic composition comprises *N. meningitidis* capsular polysaccharides from at least one, two, three or four of serogroups A, C, W and Y conjugated to a carrier protein, wherein at least one, two, three or four or each *N. meningitidis* polysaccharide is either a native polysaccharide or is sized by a factor up to ×1.5, ×2, ×3, ×4, ×5, ×6, ×7, ×8, ×9 or ×10 relative to the weight average molecular weight of the native polysaccharide.

For the purposes of the invention, "native polysaccharide" refers to a polysaccharide that has not been subjected to a process, the purpose of which is to reduce the size of the polysaccharide. A polysaccharide can become slightly reduced in size during normal purification procedures. Such a polysaccharide is still native. Only if the polysaccharide has been subjected to sizing techniques would the polysaccharide not be considered native.

For the purposes of the invention, "sized by a factor up to ×2" means that the polysaccharide is subject to a process intended to reduce the size of the polysaccharide but to retain a size more than half the size of the native polysaccharide. ×3, ×4 etc. are to be interpreted in the same way i.e. the polysaccharide is subject to a process intended to reduce the size of the polysaccharide but to retain a size more than a third, a quarter etc. the size of the native polysaccharide respectively.

In an aspect of the invention, the immunogenic composition comprises *N. meningitidis* capsular polysaccharides from at least one, two, three or four of serogroups A, C, W and Y conjugated to a carrier protein, wherein at least one, two, three or four or each *N. meningitidis* polysaccharide is native polysaccharide.

In an aspect of the invention, the immunogenic composition comprises *N. meningitidis* capsular polysaccharides from at least one, two, three or four of serogroups A, C, W and Y conjugated to a carrier protein, wherein at least one, two, three or four or each *N. meningitidis* polysaccharide is sized by a factor up to ×1.5, ×2, ×3, ×4, ×5, ×6, ×7, ×8, ×9 or ×10.

The immunogenic compositions of the invention optionally comprise conjugates of: *N. meningitidis* serogroup C capsular polysaccharide (MenC), serogroup A capsular polysaccharide (MenA), serogroup W135 capsular polysaccharide (MenW), serogroup Y capsular polysaccharide (MenY), serogroup C and Y capsular polysaccharides (MenCY), serogroup C and A capsular polysaccharides (MenAC), serogroup C and W capsular polysaccharides (MenCW), serogroup A and Y capsular polysaccharide (MenAY), serogroup A and W capsular polysaccharides (MenAW), serogroup W and Y capsular polysaccharides (Men WY), serogroup A, C and W capsular polysaccharide (MenACW), serogroup A, C and Y capsular polysaccharides (MenACY); serogroup A, W135 and Y capsular polysaccharides (MenAWY), serogroup C, W135 and Y capsular polysaccharides (MenCWY); or serogroup A, C, W135 and Y capsular polysaccharides (MenACWY). This is the definition of "one, two, three or four", or "at least one of" of serogroups A, C, W and Y, or of each *N. meningitidis* polysaccharide where mentioned herein In an embodiment, the average size (or molecular weight) of at least one, two, three, four or each *N. meningitidis* polysaccharide is 50 KDa-1500 kDa, 50 kDa-500 kDa, 50 kDa-300 KDa, 101 kDa-1500 kDa, 101 kDa-500 kDa, or 101 kDa-300 kDa as determined by MALLS.

In an embodiment, the MenA polysaccharide, where present, has a molecular weight of 50-500 kDa, 50-100 kDa, 100-500 kDa, 55-90 KDa, 60-70 kDa or 70-80 kDa or 60-80 kDa as determined by MALLS.

In an embodiment, the MenC polysaccharide, where present, has a molecular weight of 100-200 kDa, 50-100 kDa, 100-150 kDa, 101-130 kDa, 150-210 kDa or 180-210 kDa as determined by MALLS.

In an embodiment the MenY polysaccharide, where present, has a molecular weight of 60-190 kDa, 70-180 kDa, 80-170 kDa, 90-160 kDa, 100-150 kDa or 110-140 kDa, 50-100 kDa, 100-140 kDa, 140-170 kDa or 150-160 kDa as determined by MALLS.

In an embodiment the MenW polysaccharide, where present, has a molecular weight of 60-190 kDa, 70-180 kDa, 80-170 kDa, 90-160 kDa, 100-150 kDa, 110-140 kDa, 50-100 kDa or 120-140 kDa as determined by MALLS.

The molecular weight or average molecular weight of a polysaccharide herein refers to the weight-average molecular weight (Mw) of the polysaccharide measured prior to conjugation and is measured by MALLS.

The MALLS technique is well known in the art and is typically carried out as described in example 2. For MALLS analysis of meningococcal saccharides, two columns (TSKG6000 and 5000PWx1 TOSOH Bioscience) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm).

In an embodiment the *N. meningitidis* polysaccharides are native polysaccharides or native polysaccharides which have reduced in size during a normal extraction process.

In an embodiment, the *N. meningitidis* polysaccharides are sized by mechanical cleavage, for instance by microfluidisation or sonication. Microfluidisation and sonication have the advantage of decreasing the size of the larger native polysaccharides sufficiently to provide a filterable conjugate. Sizing is by a factor of no more than ×20, ×10, ×8, ×6, ×5, ×4, ×3, ×2 or ×1.5.

In an embodiment, the immunogenic composition comprises *N. meningitidis* conjugates that are made from a mixture of native polysaccharides and polysaccharides that are sized by a factor of no more than ×20. For example, polysaccharides from MenC and/or MenA are native. For example, polysaccharides from MenY and/or MenW are sized by a factor of no more than ×20, ×10, ×8, ×6, ×5, ×4, ×3, ×2 or ×1.5. For example, an immunogenic composition contains a conjugate made from MenY and/or MenW and/or MenC and/or MenA which is sized by a factor of no more then ×20, ×10, ×8, ×6, ×5, ×4, ×3, ×2 or ×1.5 and/or is microfluidised. For example, an immunogenic composition contains a conjugate made from native MenA and/or MenC and/or MenW and/or MenY. For example, an immunogenic composition comprises a conjugate made from native MenC. For example, an immunogenic composition comprises a conjugate made from native MenC and MenA which is sized by a factor of no more than ×20, ×10, ×8, ×6, ×5, ×4, ×3, ×2 or ×1.5 and/or is microfluidised. For example, an immunogenic composition comprises a conjugate made from native MenC and MenY which is sized by a factor of no more than ×20, ×10, ×8, ×6, ×5, ×4, ×3, ×2 or ×1.5 and/or is microfluidised.

In an embodiment, the polydispersity of the polysaccharide is 1-1.5, 1-1.3, 1-1.2, 1-1.1 or 1-1.05 and after conjugation to a carrier protein, the polydispersity of the conjugate is 1.0-2.5, 1.0-2.0. 1.0-1.5, 1.0-1.2, 1.5-2.5, 1.7-2.2 or 1.5-2.0. All polydispersity measurements are by MALLS.

Polysaccharides are optionally sized up to 1.5, 2, 4, 6, 8, 10, 12, 14, 16, 18 or 20 times from the size of the polysaccharide isolated from bacteria.

In an embodiment, the immunogenic composition of the invention further comprises an antigen from *N. meningitidis* serogroup B. The antigen is optionally a capsular polysaccharide from *N. meningitidis* serogroup B (MenB) or a sized polysaccharide or oligosaccharide derived therefrom. The antigen is optionally an outer membrane vesicle preparation from *N. meningitidis* serogroup B as described in EP301992, WO 01/09350, WO 04/14417, WO 04/14418 and WO 04/14419.

In an embodiment, the immunogenic composition of the invention further comprises a *H. influenzae* b (Hib) capsular saccharide conjugated to a carrier protein.

The *N. meningitidis* polysaccharide(s) (and optionally Hib capsular saccharide) included in pharmaceutical compositions of the invention are conjugated to a carrier protein such as tetanus toxoid, tetanus toxoid fragment C, non-toxic mutants of tetanus toxin, diphtheria toxoid, CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. Nos. 4,709,017 or 4,950,740; mutation of at least one or more residues Lys 516, Lys 526, Phe 530 and/or Lys 534 and other mutations disclosed in U.S. Pat. Nos. 5,917,017 or 6,455,673; or fragment disclosed in U.S. Pat. No. 5,843,711], pneumococcal pneumolysin, OMPC (meningococcal outer membrane protein—usually extracted from *N. meningitidis* serogroup B—EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998) pneumolysin (Kuo et al (1995) Infect Immun 63; 2706-13), iron uptake proteins (WO 01/72337), toxin A or B of *C. difficile* (WO 00/61761) or Protein D (EP594610 and WO 00/56360).

In an embodiment, the immunogenic composition of the invention uses the same carrier protein (independently) in at least two, three, four or each of the *N. meningitidis* polysaccharides. In an embodiment where Hib is present, Hib may be conjugated to the same carrier protein as the at least one, two, three, four or each of the *N. meningitidis* polysaccharides. For example, 1, 2, 3 or 4 of the *N. meningitidis* polysaccharides are independently conjugated to tetanus toxoid to make 1, 2, 3 or 4 conjugates.

In an embodiment, a single carrier protein may carry more than one saccharide antigen (WO 04/083251). For example, a single carrier protein might be conjugated to MenA and MenC; MenA and MenW; MenA and MenY; MenC and MenW; MenC and MenY; Men W and MenY; MenA, MenC and MenW; MenA, MenC and MenY; MenA, MenW and MenY; MenC, MenW and MenY; MenA, MenC, MenW and MenY; Hib and MenA; Hib and MenC; Hib and MenW; or Hib and MenY.

In an embodiment, the immunogenic composition of the invention comprises a *N. meningitidis* polysaccharide conjugated to a carrier protein selected from the group consisting of TT, DT, CRM197, fragment C of TT and protein D.

In an embodiment, the immunogenic composition of the invention comprises a Hib saccharide conjugated to a carrier protein selected from the group consisting of TT, DT, CRM197, fragment C of TT and protein D.

The immunogenic composition of the invention optionally comprises at least one meningococcal saccharide (for example MenA; MenC; MenW; MenY; MenA and MenC; MenA and MenW; MenA and MenY; MenC and Men W; Men C and MenY; Men W and MenY; MenA, MenC and MenW; MenA, MenC and MenY; MenA, MenW and MwnY; MenC, MenW and MenY or MenA, MenC, MenW and MenY) conjugate having a ratio of Men saccharide to carrier protein of between 1:5 and 5:1, between 1:2 and 5:1, between 1:0.5 and 1:2.5 or between 1:1.25 and 1:2.5 (w/w).

The immunogenic composition of the invention optionally comprises a Hib saccharide conjugate having a ratio of Hib to carrier protein of between 1:5 and 5:1; 1:2 and 2:1; 1:1 and 1:4; 1:2 and 1:3.5; or around or exactly 1:2.5 or 1:3 (w/w). By 'around' it is meant within 10% of the stated ratio.

The ratio of saccharide to carrier protein (w/w) in a conjugate may be determined using the sterilized conjugate. The amount of protein is determined using a Lowry assay (for example Lowry et al (1951) J. Biol. Chem. 193, 265-275 or Peterson et al Analytical Biochemistry 100, 201-220 (1979)) and the amount of saccharide is determined using ICP-OES (inductively coupled plasma-optical emission spectroscopy) for MenA, DMAP assay for MenC and Resorcinol assay for MenW and MenY (Monsigny et al (1988) Anal. Biochem. 175, 525-530).

In an embodiment, the immunogenic composition of the invention the *N. meningitidis* polysaccharide(s) and/or the Hib saccharide is conjugated to the carrier protein via a linker, for instance a bifunctional linker. The linker is optionally heterobifunctional or homobifunctional, having for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH. Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. Nos. 4,673,574, 4,808,700), hexane diamine and 6-aminocaproic acid (U.S. Pat. No. 4,459,286).

The polysaccharide conjugates present in the immunogenic compositions of the invention may be prepared by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a holoacetylated carrier protein (for example using iodoacetimide or N-succinimidyl bromoacetatebromoacetate). Optionally, the cyanate ester (optionally made by CDAP chemistry) is coupled with hexane diamine or ADH and the amino-derivatised saccharide is conjugated to the carrier protein using using carbodiimide (e.g. EDAC or EDC) chemistry. Such conjugates are described in PCT published application WO 93/15760 Uniformed Services University and WO 95/08348 and WO 96/29094.

Other suitable techniques use carbiinides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (Bethell et al J. Biol. Chem. 1979, 254; 2572-4, Hearn et al J. Chromatogr. 1981. 218; 509-18) followed by reaction of with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated saccharide derivatised with adipic acid hydrazide (ADH) to the protein carrier by Carbodiimide condensation (Chu C. et al Infect. Immunity, 1983 245 256), for example using EDAC.

In an embodiment, a hydroxyl group (optionally an activated hydroxyl group for example a hydroxyl group activated by a cyanate ester) on a saccharide is linked to an amino or carboxylic group on a protein either directly or indirectly (through a linker). Where a linker is present, a hydroxyl group on a saccharide is optionally linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, the Hib or N. meningitidis capsular polysaccharide(s) is conjugated to the linker first before the linker is conjugated to the carrier protein.

In an embodiment, the Hib saccharide, where present, is conjugated to the carrier protein using CNBr, or CDAP, or a combination of CDAP and carbodiimide chemistry (such as EDAC), or a combination of CNBr and carbodiimide chemistry (such as EDAC). Optionally Hib is conjugated using CNBr and carbodiimide chemistry, optionally EDAC. For example, CNBr is used to join the saccharide and linker and then carbodiimide chemistry is used to join linker to the protein carrier.

In an embodiment, at least one of the N. meningitidis capsular polysaccharides is directly conjugated to a carrier protein; optionally Men W and/or MenY and/or MenC saccharide(s) is directly conjugated to a carrier protein. For example MenW; MenY; MenC; MenW and MenY; MenW and MenC; MenY and MenC; or MenW, MenY and MenC are directly linked to the carrier protein. Optionally the at least one of the N. meningitidis capsular polysaccharides is directly conjugated by CDAP. For example MenW; MenY; MenC; MenW and MenY; MenW and MenC; MenY and MenC; or MenW, MenY and MenC are directly linked to the carrier protein by CDAP (see WO 95/08348 and WO 96/29094). In an embodiment, all N. meningitidis capsular polysaccharides are conjugated to tetanus toxoid.

Optionally the ratio of Men W and/or Y saccharide to carrier protein is between 1:0.5 and 1:2 (w/w) and/or the ratio of MenC saccharide to carrier protein is between 1:0.5 and 1:4 or 1:1.25-1:1.5 or 1:0.5 and 1:1.5 (w/w), especially where these saccharides are directly linked to the protein, optionally using CDAP.

In an embodiment, at least one of the N. meningitidis capsular polysaccharide(s) is conjugated to the carrier protein via a linker, for instance a bifunctional linker. The linker is optionally heterobifunctional or homobifunctional, having for example a reactive amine group and a reactive carboxylic acid group, 2 reactive amine groups or 2 reactive carboxylic acid groups. The linker has for example between 4 and 20, 4 and 12, 5 and 10 carbon atoms. A possible linker is ADH.

In an embodiment, MenA; MenC; or MenA and MenC is conjugated to a carrier protein (for example tetanus toxoid) via a linker.

In an embodiment, at least one N. meningitidis polysaccharide is conjugated to a carrier protein via a linker using CDAP and EDAC. For example, MenA; MenC; or MenA and MenC are conjugated to a protein via a linker (for example those with two hydrozino groups at its ends such as ADH) using CDAP and EDAC as described above. For example, CDAP is used to conjugate the saccharide to a linker and EDAC is used to conjugate the linker to a protein. Optionally the conjugation via a linker results in a ratio of polysaccharide to carrier protein of of between 1:0.5 and 1:6; 1:1 and 1:5 or 1:2 and 1:4, for MenA; MenC; or MenA and MenC.

In an embodiment, the MenA capsular polysaccharide, where present is is at least partially O-acetylated such that at least 50%, 60%, 70%, 80%, 90%, 95% or 98% of the repeat units are O-acetylated at at least one position. O-acetylation is for example present at least at the O-3 position of at least 50%, 60%, 70%, 80%, 90%, 95% or 98% of the repeat units.

In an embodiment, the MenC capsular polysaccharide, where present is is at least partially O-acetylated such that at least 30%, 40%, 50%, 60%, 70%, 80%, 90%, 95% or 98% of ($\alpha 2 \rightarrow 9$)-linked NeuNAc repeat units are O-acetylated at at least one or two positions. O-acetylation is for example present at the O-7 and/or O-8 position of at least 30%. 40%, 50%, 60%, 70%, 80%, 90%, 95% or 98% of the repeat units.

In an embodiment, the MenW capsular polysaccharide, where present is is at least partially O-acetylated such that at least 30%, 40%, 50%, 60%, 70%, 80%, 90%, 95% or 98% of the repeat units are O-acetylated at at least one or two positions. O-acetylation is for example present at the O-7 and/or O-9 position of at least 30%. 40%, 50%, 60%, 70%, 80%, 90%, 95% or 98% of the repeat units.

In an embodiment, the MenY capsular polysaccharide, where present is at least partially O-acetylated such that at least 20%, 30%, 40%, 50%, 60%, 70%, 80%, 90%, 95% or 98% of the repeat units are O-acetylated at at least one or two positions. O-acetylation is present at the 7 and/or 9 position of at least 20%, 30%, 40%, 50%, 60%, 70%, 80%, 90%, 95% or 98% of the repeat units.

The percentage of O-acetylation refers to the percentage of the repeat units containing O-acetylation. This may be measured in the polysaccharide prior to conjugate and/or after conjugation.

In a further embodiment, the immunogenic composition of the invention comprises a Hib saccharide conjugate and at least two N. meningitidis polysaccharide conjugates wherein the Hib conjugate is present in a lower saccharide dose than the mean saccharide dose of the at least two N. meningitidis polysaccharide conjugates. Alternatively, the Hib conjugate is present in a lower saccharide dose than the saccharide dose of each of the at least two N. meningitidis polysaccharide conjugates. For example, the dose of the Hib conjugate may be at least 10%, 20%, 30%, 40%, 50%, 60%, 70% or 80% lower than the mean or lowest saccharide dose of the at least two further N. meningitidis polysaccharide conjugates.

The term "saccharide" includes polysaccharides or oligosaccharides. Polysaccharides are isolated from bacteria or isolated from bacteria and sized to some degree by known methods (see for example EP497524 and EP497525) and optionally by microfluidisation. Polysaccharides can be sized in order to reduce viscosity in polysaccharide samples and/or to improve filterability for conjugated products. Oligosaccharides are characterised by typically being hydrolysed polysaccharides with a low number of repeat units (typically 5-30 repeat units).

The mean dose is determined by adding the doses of all the further polysaccharides and dividing by the number of further polysaccharides. Further polysaccharides are all the polysaccharides within the immunogenic composition apart from Hib and can include N. meningitidis capsular polysaccharides. The "dose" is in the amount of immunogenic composition or vaccine that is administered to a human.

A Hib saccharide is the polyribosyl phosphate (PRP) capsular polysaccharide of Haemophilus influenzae type b or an oligosaccharide derived therefrom.

'At least two further bacterial saccharide conjugates' is to be taken to mean at least two further bacterial saccharide conjugates in addition to a Hib conjugate. The at least two further bacterial conjugates may include N. meningitidis capsular polysaccharide conjugates.

The immunogenic compositions of the invention may comprise further saccharide conjugates derived from one or more of Neisseria meningitidis, Streptococcus pneumoniae, Group A Streptococci, Group B Streptococci, S. typhi, Staphylococcus aureus or Staphylococcus epidermidis. In an embodiment, the immunogenic composition comprises capsular polysaccharides or oligosaccharides derived from one or more of serogroups A, C, W135 and Y of Neisseria meningitidis. A further embodiment comprises capsular polysaccharides or oligosaccharides derived from Streptococcus pneumoniae. The pneumococcal capsular polysaccharide or oligosaccharide antigens are optionally selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F (optionally from serotypes 1, 3, 4, 5, 6B, 7F, 9V, 14, 18C, 19F and 23F). A further embodiment comprises the Type 5, Type 8 or 336 capsular polysaccharides or oligosaccharides of Staphylococcus aureus. A further embodiment comprises the Type I, Type II or Type III capsular polysaccharides of Staphylococcus epidermidis. A further embodiment comprises the Vi saccharide (poly or oligosaccharide) from S. typhi. A further embodiment comprises the Type Ia, Type Ic, Type II, Type III or Type V capsular polysaccharides or oligosaccharides of Group B streptocoocus. A further embodiment comprises the capsular polysaccharides or oligosaccharides of Group A streptococcus, optionally further comprising at least one M protein and optionally multiple types of M protein.

In an embodiments, the immunogenic composition of the invention contains each N. meningitidis capsular polysaccharide at a dose of between 0.1-20 μg; 1-10 μg; 2-10 μg, 2.5-5 μg, around or exactly 5 μg; or around or exactly 2.5 μg.

In an embodiment, the immunogenic composition of the invention for example contains the Hib saccharide conjugate at a saccharide dose between 0.1 and 9 μg; 1 and 5 μg or 2 and 3 μg or around or exactly 2.5 μg and each of the N. meningitidis polysaccharide conjugates at a saccharide dose of between 2 and 20 μg, 3 and 10 μg, or between 4 and 7 μg or around or exactly 5 μg.

"Around" or "approximately" are defined as within 10% more or less of the given figure for the purposes of the invention.

In an embodiment, the immunogenic composition of the invention contains a saccharide dose of the Hib saccharide conjugate which is for example less than 90%, 80%, 75%, 70%, 60%, 50%, 40%, 30%, 20% or 10% of the mean saccharide dose of at least two, three, four or each of the N. meningitidis polysaccharide conjugates. The saccharide dose of the Hib saccharide is for example between 20% and 60%, 30% and 60%, 40% and 60% or around or exactly 50% of the mean saccharide dose of at least two, three, four or each of the N. meningitidis polysaccharide conjugates.

In an embodiment, the immunogenic composition of the invention contains a saccharide dose of the Hib saccharide conjugate which is for example less than 90%, 80%, 75%, 70%, 60%, 50%, 40%, 30%, 20% or 10% of the lowest saccharide dose of the at least two, three, four or each of the N. meningitidis polysaccharide conjugates. The saccharide dose of the Hib saccharide is for example between 20% and 60%, 30% and 60%, 40% and 60% or around or exactly 50% of the lowest saccharide dose of the at least two, three, four or each of the N. meningitidis polysaccharide conjugates.

In an embodiment of the invention, the saccharide dose of each of the at least two, three, four or each of the N. meningitidis polysaccharide conjugates is optionally the same, or approximately the same.

Examples of immunogenic compositions of the invention are compositions consisting of or comprising:

Hib conjugate and MenA conjugate and MenC conjugate, optionally at saccharide dose ratios of 1:2:2, 1:2:1, 1:4:2, 1:6:3, 1:3:3, 1:4:4, 1:5:5, 1:6:6 (w/w). Optionally, the saccharide dose of MenA is greater than the saccharide dose of MenC.

Hib conjugate and MenC conjugate and MenY conjugate, optionally at saccharide dose ratios of 1:2:2, 1:2:1, 1:4:2, 1:4:1, 1:8:4, 1:6:3, 1:3:3, 1:4:4, 1:5:5, 1:6:6 (w/w). Optionally, the saccharide dose of MenC is greater than the saccharide dose of MenY.

Hib conjugate and MenC conjugate and MenW conjugate, optionally at saccharide dose ratios of 1:2:2, 1:2:1, 1:4:2, 1:4:1, 1:8:4, 1:6:3, 1:3:3, 1:4:4, 1:5:5, 1:6:6 (w/w). Optionally the saccharide dose of MenC is greater than the saccharide dose of MenW.

Hib conjugate and MenA conjugate and MenW conjugate, optionally at saccharide dose ratios of 1:2:2, 1:2:1, 1:4:2, 1:4:1, 1:8;4, 1:6:3, 1:3:3, 1:4:4, 1:5:5, 1:6:6 (w/w). Optionally, the saccharide dose of MenA is greater than the saccharide dose of MenW.

Hib conjugate and MenA conjugate and MenY conjugate, optionally at saccharide dose ratios of 1:2:2, 1:2:1, 1:4:2, 1:4:1, 1:8:4, 1:6:3, 1:3:3, 1:4:4, 1:5:5, 1:6:6 (w/w). Optionally the saccharide dose of MenA is greater than the saccharide dose of MenY.

Hib conjugate and MenW conjugate and MenY conjugate, optionally at saccharide dose ratios of 1:2:2, 1:2:1, 1:1:2, 1:4:2, 1:2:4, 1:4:1, 1:1:4, 1:3;6, 1:1:3, 1:6:3, 1:3:3, 1:4:4, 1:5:5, 1:6:6 (w/w). Optionally the saccharide dose of MenY is greater than the saccharide dose of MenW.

MenA, MenC, MenW and MenY at saccharide dose ratios of 1:1:1:1 or 2:1:1:1 or 1:2:1:1 or 2:2:1:1 or 1:3:1:1 or 1:4:1:1 (w/w).

A further aspect of the invention is a vaccine comprising the immunogenic composition of the invention and a pharmaceutically acceptable excipient.

In an embodiment, the immunogenic composition of the invention is buffered at, or adjusted to, between pH 7.0 and 8.0, pH 7.2 and 7.6 or around or exactly pH 7.4.

The immunogenic composition or vaccines of the invention are optionally lyophilised in the presence of a stabilising agent for example a polyol such as sucrose or trehalose.

Optionally, the immunogenic composition or vaccine of the invention contains an amount of an adjuvant sufficient to enhance the immune response to the immunogen. Suitable adjuvants include, but are not limited to, aluminium salts (aluminium phosphate or aluminium hydroxide), squalene mixtures (SAF-1), muramyl peptide, saponin derivatives, *mycobacterium* cell wall preparations, monophosphoryl lipid A, mycolic acid derivatives, non-ionic block copolymer surfactants, Quil A, cholera toxin B subunit, polyphosphazene and derivatives, and immunostimulating complexes (ISCOMs) such as those described by Takahashi et al. (1990) Nature 344:873-875.

For the *N. meningitidis* or HibMen combinations discussed above, it may be advantageous not to use any aluminium salt adjuvant or any adjuvant at all.

As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, route of administrations and the number of immunising dosages to be administered. Such factors are known in the vaccine art and it is well within the skill of immunologists to make such determinations without undue experimentation.

The active agent can be present in varying concentrations in the pharmaceutical composition or vaccine of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is optionally one which will provide a single therapeutically effective dosage. For bioactive substances, the minimum concentration is an amount necessary for bioactivity upon reconstitution and the maximum concentration is at the point at which a homogeneous suspension cannot be maintained. In the case of single-dosed units, the amount is that of a single therapeutic application. Generally, it is expected that each dose will comprise 1-100 µg of protein antigen, optionally 5-50 µg or 5-25 µg. Examples of doses of bacterial saccharides are 10-20 µg, 5-10 µg, 2.5-5 µg or 1-2.5 µg. The preferred amount of the substance varies from substance to substance but is easily determinable by one of skill in the art.

The vaccine preparations of the present invention may be used to protect or treat a mammal (for example a human patient) susceptible to infection, by means of administering said vaccine via systemic or mucosal route. A human patient is optionally an infant (under 12 months), a toddler (12-24, 12-16 or 12-14 months), a child (2-10, 3-8 or 3-5 years) an adolescent (12-25, 14-21 or 15-19 years) or an adult (any age over 12, 15, 18 or 21). These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance if saccharides are present in a vaccine these could be administered separately at the same time or 1-2 weeks after the administration of a bacterial protein vaccine for optimal coordination of the immune responses with respect to each other). In addition to a single route of administration, 2 different routes of administration may be used. For example, viral antigens may be administered ID (intradermal), whilst bacterial proteins may be administered IM (intramuscular) or IN (intranasal). If saccharides are present, they may be administered IM (or ID) and bacterial proteins may be administered IN (or ID). In addition, the vaccines of the invention may be administered IM for priming doses and IN for booster doses.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

A further aspect of the invention is a vaccine kit for concomitant or sequential administration comprising two multi-valent immunogenic compositions for conferring protection in a host against disease caused by *Bordetella pertussis, Clostridium tetani, Corynebacterium diphtherias* and *Neisseria meningitidis* and optionally *Haemophilus influenzae*. For example, the kit optionally comprises a first container comprising one or more of:
  tetanus toxoid (TT),
  diphtheria toxoid (DT), and
  whole cell or acellular pertussis components
  and a second container comprising either:
  *N. meningitidis* capsular polysaccharides from at least one, two, three or four of serogroups A, C, W and Y conjugated to a carrier protein, wherein the average size of each *N. meningitidis* polysaccharide is above 50 kDa, 75 kDa, 100 kDa, 110 kDa, 120 kDa or 130 kDa, optionally lyophilised.
  or
  Hib saccharide conjugate, and
  *N. meningitidis* capsular polysaccharides from at least one, two, three or four of serogroups A, C, W and Y conjugated to a carrier protein, wherein the average size of each *N. meningitidis* polysaccharide is above 50 kDa, 75 kDa, 100 kDa, 110 kDa, 120 kDa or 130 kDa, optionally lyophilised.

Formulation examples of the Hib conjugate and the *N. meningitidis* polysaccharide conjugates are as described above.

A further aspect of the invention is a vaccine kit for concomitant or sequential administration comprising two multi-valent immunogenic compositions for conferring protection in a host against disease caused by *Streptococcus pneumoniae* and *Neisseria meningitidis* and optionally *Haemophilus influenzae*. For example, the kit optionally comprises a first container comprising:

one or more conjugates of a carrier protein and a capsular saccharide from *Streptococcus pneumoniae* [where the capsular saccharide is optionally from a pneumococcal serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F].

and a second container comprising either:

*N. meningitidis* capsular polysaccharides from at least one, two, three or four of serogroups A, C, W and Y conjugated to a carrier protein, wherein the average size of each *N. meningitidis* polysaccharide is above 50 kDa, 75 kDa, 100 kDa, 110 kDa, 120 kDa or 130 kDa, optionally lyophilised.

or

Hib saccharide conjugate, and

*N. meningitidis* capsular polysaccharides from at least one, two, three or four of serogroups A, C, W and Y conjugated to a carrier protein, wherein the average size of each *N. meningitidis* polysaccharide is above 50 kDa, 75 kDa, 100 kDa, 110 kDa, 120 kDa or 130 kDa, optionally lyophilised.

Examples of the Hib conjugate and the *N. meningitidis* polysaccharide conjugates are as described above.

Typically the *Streptococcus pneumoniae* vaccine in the vaccine kit of the present invention will comprise saccharide antigens (optionally conjugated), wherein the polysaccharides are derived from at least four serotypes of pneumococcus chosen from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. Optionally the four serotypes include 6B, 14, 19F and 23F. Optionally, at least 7 serotypes are included in the composition, for example those derived from serotypes 4, 6B, 9V, 14, 18C, 19F, and 23F. Optionally more than 7 serotypes are included in the composition, for instance at least 10, 11, 12, 13 or 14 serotypes. For example the composition in one embodiment includes 11 capsular polysaccharides derived from serotypes 1, 3, 4, 5, 6B, 7F, 9V, 14, 18C, 19F and 23F (optionally conjugated). In an embodiment of the invention at least 13 polysaccharide antigens (optionally conjugated) are included, although further polysaccharide antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

The pneumococcal saccharides are independently conjugated to any known carrier protein, for example CRM197, tetanus toxoid, diphtheria toxoid, protein D or any other carrier proteins as mentioned above.

Optionally, the vaccine kits of the invention comprise a third component. For example, the kit optionally comprises a first container comprising one or more of:

tetanus toxoid (TT),
diphtheria toxoid (DT), and
whole cell or acellular pertussis components and a second container comprising:

one or more conjugates of a carrier protein and a capsular saccharide from *Streptococcus pneumoniae* [where the capsular saccharide is optionally from a pneumococcal serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F].

and a third container comprising:

*N. meningitidis* capsular polysaccharides from at least one, two, three or four of serogroups A, C, W and Y conjugated to a carrier protein, wherein the average size of each *N. meningitidis* polysaccharide is above 50 kDa, 75 kDa, 100 kDa, 110 kDa, 120 kDa or 130 kDa, optionally lyophilized.

or

Hib saccharide conjugate, and

*N. meningitidis* capsular polysaccharides from at least one, two, three or four of serogroups A, C, W and Y conjugated to a carrier protein, wherein the average size of each *N. meningitidis* polysaccharide is above 50 kDa, 75 kDa, 100 kDa, 110 kDa, 120 kDa or 130 kDa, optionally lyophilised.

Immunogenic compositions comprising meningococcal conjugates, for example HibMenC, HibMenAC, HibMenAW, HibMenAY, HibMenCW, HibMenCY, HibMenWY, MenAC, MenAW, MenAY, MenCW, MenCY, MenWY or MenACWY, including kits of similar composition to those described above, optionally comprise antigens from measles and/or mumps and/or rubella and/or varicella. For example, the meningococcal immunogenic composition contains antigens from measles, mumps and rubella or measles, mumps, rubella and varicella. In an embodiment, these viral antigens are optionally present in the same container as the meningococcal and/or Hib saccharide conjugate(s). In an embodiment, these viral antigens are lyophilised.

A further aspect of the invention is a process for making the immunogenic composition of the invention, comprising the step of mixing *N. meningitidis* capsular polysaccharides from at least one, two or three of serogroups A, C, W and Y conjugated to a carrier protein with a bacterial saccharide conjugate, wherein the average size of each *N. meningitidis* polysaccharide is above 50 kDa, 75 kDa, 100 kDa, 110 kDa, 120 kDa or 130 kDa.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

A further aspect of the invention is a method of immunising a human host against disease caused by *N. meningitidis* and optionally *Haemophilus influenzae* infection comprising administering to the host an immunoprotective dose of the immunogenic composition or vaccine or kit of the invention.

A further aspect of the invention is an immunogenic composition of the invention for use in the treatment or prevention of disease caused by *N. meningitidis* and optionally *Haemophilus influenzae* infection.

A further aspect of the invention is use of the immunogenic composition or vaccine or kit of the invention in the manufacture of a medicament for the treatment or prevention of diseases caused by *N. meningitidis* and optionally *Haemophilus influenzae* infection.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLES

Example 1

Preparation of Polysaccharide Conjugates

The covalent binding of *Haemophilus influenzae* (Hib) PRP polysaccharide to TT was carried out by a coupling chemistry developed by Chu et al (Infection and Immunity 1983, 40 (1); 245-256). Hib PRP polysaccharide was activated by adding CNBr and incubating at pH10.5 for 6 minutes. The pH was lowered to pH8.75 and adipic acid dihyrazide (ADH) was added and incubation continued for a further 90 minutes. The activated PRP was coupled to purified tetanus toxoid via carbodiimide condensation using 1-ethyl-3-(3-dimethyl-aminopropyl)carbodiimide (EDAC). EDAC was added to the activated PRP to reach a final ratio of 0.6 mg EDAC/mg activated PRP. The pH was adjusted to 5.0 and purified tetanus toxoid was added to reach 2 mg TT/mg activated PRP. The resulting solution was left for three days with mild stirring. After filtration through a 0.45 µm membrane, the conjugate was purified on a sephacryl S500HR (Pharmacia, Sweden) column equilibrated in 0.2M NaCl.

MenC-TT conjugates were produced using native polysaccharides (of over 150 kDa as measured by MALLS). MenA-TT conjugates were produced using either native polysaccharide or slightly microfluidised polysaccharide of over 60 kDa as measured by the MALLS method of example 2. MenW and MenY-TT conjugates were produced using sized polysaccharides of around 100-200 kDa as measured by MALLS (see example 2). Sizing was by microfluidisation using a homogenizer Emulsiflex C-50 apparatus. The polysaccharides were then filtered through a 0.2 µm filter.

Activation and coupling were performed as described in WO96/29094 and WO00/56360. Briefly, the polysaccharide at a concentration of 10-20 mg/ml in 2M NaCl pH 5.5-6.0 was mixed with CDAPsolution (100 mg/ml freshly prepared in acetonitrile/WFI, 50/50) to a final CDAP/polysaccharide ratio of 0.75/1 or 1.5/1. After 1.5 minutes, the pH was raised with sodium hydroxide to pH10.0. After three minutes tetanus toxoid was added to reach a protein/polysaccharide ratio of 1.5/1 for MenW, 1.2/1 for MenY, 1.5/1 for MenA or 1.5/1 for MenC. The reaction continued for one to two hours.

After the coupling step, glycine was added to a final ratio of glycine/PS (w/w) of 7.5/1 and the pH was adjusted to pH9.0. The mixture was left for 30 minutes. The conjugate was clarified using a 10 µm Kleenpak filter and was then loaded onto a Sephacryl S400HR column using an elution buffer of 150 mM NaCl, 10 mM or 5 mM Tris pH7.5. Clinical lots were filtered on an Opticap 4 sterilizing membrane. The resultant conjugates had an average polysaccharide:protein ratio of 1:1-1:5 (w/w).

In order to conjugate MenA capsular polysaccharide to tetanus toxoid via a spacer, the following method was used. The covalent binding of the polysaccharide and the spacer (ADH) is carried out by a coupling chemistry by which the polysaccharide is activated under controlled conditions by a cyanylating agent, 1-cyano-4-dimethylamino-pyridinium tetrafluoroborate (CDAP). The spacer reacts with the cyanylated PS through its hydrazino groups, to form a stable isourea link between the spacer and the polysaccharide.

A 10 mg/ml solution of MenA was treated with a freshly prepared 100 mg/ml solution of CDAP in acetonitrile/water (50/50 (v/v)) to obtain a CDAP/MenA ratio of 0.75 (w/w). After 1.5 minutes, the pH was raised to pH 10.0. Three minutes later, ADH was added to obtain an ADH/MenA ratio of 8.9. The pH of the solution was decreased to 8.75 and the reaction proceeded for 2 hours.

Prior to the conjugation reaction, the purified TT solution and the PSA solution were diluted to reach a concentration of 10 mg/ml for $PSA_{AH}$ and 10 mg/ml for TT.

EDAC was added to the $PS_{AH}$ solution in order to reach a final ratio of 0.9 mg EDAC/mg $PSA_{AH}$. The pH was adjusted to 5.0. The purified tetanus toxoid was added with a peristaltic pump (in 60 minutes) to reach 2 mg TT/mg $PSA_{AH}$. The resulting solution was left 60 min at +25° C. under stirring to obtain a final coupling time of 120 min. The conjugate was clarified using a 10 µm filter and was purified using a Sephacryl S400HR column.

Example 2

Determination of Molecular Weight Using MALLS

Detectors were coupled to a HPLC size exclusion column from which the samples were eluted. On one hand, the laser light scattering detector measured the light intensities scattered at 16 angles by the macromolecular solution and on the other hand, an interferometric refractometer placed on-line allowed the determination of the quantity of sample eluted. From these intensities, the size and shape of the macromolecules in solution can be determined.

The mean molecular weight in weight ($M_w$) is defined as the sum of the weights of all the species multiplied by their respective molecular weight and divided by the sum of weights of all the species.

a) Weight-average molecular weight:

$$M_w = \frac{\sum W_i \cdot M_i}{\sum W_i} = \frac{m_2}{m_1}$$

b) Number-average molecular weight:

$$M_n = \frac{\sum N_i \cdot M_i}{\sum N_i} = \frac{m_1}{m_0}$$

c) Root mean square radius: -Rw- and $R^2w$ is the square radius defined by:

$$R^2w \text{ or } (r^2)w = \frac{\sum m_i \cdot r_i^2}{\sum m_i}$$

(-$m_i$- is the mass of a scattering centre i and -$r_i$- is the distance between the scattering centre i and the center of gravity of the macromolecule).

d) The polydispersity is defined as the ratio -Mw/Mn-.

Meningococcal polysaccharides were analysed by MALLS by loading onto two HPLC columns (TSKG6000 and 5000PWx1) used in combination. 25 µl of the polysaccharide were loaded onto the column and was eluted with 0.75 ml of filtered water. The polyaccharides are detected using a light scattering detector (Wyatt Dawn DSP equipped with a 10 mW argon laser at 488 nm) and an inferometric refractometer (Wyatt Otilab DSP equipped with a P100 cell and a red filter at 498 nm).

The molecular weight polydispersities and recoveries of all samples were calculated by the Debye method using a polynomial fit order of 1 in the Astra 4.72 software.

Example 3

Clinical Trial Comparing Immunisation with Meningitec or a Larger Sized MenC-TT Conjugate A phase II, open, controlled study was carried out to compare GSK Biologicals meningococcal serogroup C conjugate vaccine (MenC) with GSK Biological's *Haemophilus influenzae* b-meningococcal serogroup C conjugate vaccine (Hib-MenC) or Meningitec®. Each dose of Meningitec® contains 10 μg of meningococcal serogroup C oligosaccharide conjugated to 15 μg of CRM197 and is produced by Wyeth. The GSK MenC conjugates contained native polysaccharides of about 200 kDa conjugated to tetanus toxoid (TT).

The study consisted of five groups, each planned to contain 100 subjects, allocated to two parallel arms as follows:

In this present study, all subjects in both arms received one-fifth (⅕) of a dose of Mencevax™ ACWY and a concomitant dose of Infanrix™ hexa at 12-15 months of age (Study Month 0). Two blood samples were collected from all subjects (Study Month 0 and Study Month 1). Arm 1 consisted of four groups from a primary vaccination study who were primed at their age of 3, 4 and 5 months with the following vaccines:

Group K: MenC (10 μg), non-adsorbed onto aluminium salts (non-ads), tetanus toxoid (TT) conjugate and Infanrix™ hexa (MenC10-TT+Infanrix™ hexa)

Group L: Hib (10 μg)-MenC (10 μg), non-ads TT conjugate and Infanrix™ penta (Hib10-MenC10-TT+Infanrix™ penta)

Group M: Hib (5 μg)-MenC (5 μg), non-ads, TT conjugate and Infanrix™ penta (Hib5-MenC5-TT+Infanrix™ penta)

Group N: Meningitec™ and Infanrix™ hexa (Meningitec™+Infanrix™ hexa)

The two Hib-MenC-TT vaccine groups (Groups L and M) were kept blinded in the booster study as to the exact formulation of the candidate vaccine.

Arm 2-(Group O) consisted of age-matched subjects not previously vaccinated with a meningococcal serogroup C vaccine (naïve) but who had received routine pediatric vaccines according to the German Permanent Commission on Immunization.

Criteria for Evaluation:

Immunogenicity:

Determination of bactericidal antibody titers against meningococcal C (SBA-MenC) by a bactericidal test (cutoff: a dilution of 1:8) and ELISA measurement of antibodies against meningococcal serogroup C (assay cut-off: 0.3 μg/ml), the Hib polysaccharide PRP (assay cut-off: 0.15 μg/ml) and tetanus toxoid (assay cut-off: 0.1 IU/ml) in blood samples obtained prior to vaccination and approximately one month after vaccination in all subjects.

Statistical Methods:

Demographics:

Determination of mean age in months (with median, range and standard deviation [SD]), and racial and gender composition of the ATP and Total vaccinated cohorts.

Immunogenicity:

Two analyses of immunogenicity were performed based on the ATP cohort for immunogenicity (for analyses of immune memory and booster response) or the ATP cohort for safety (for analysis of persistence). These included:

Evaluation of immune memory for MenC and booster response for Hib and Tetanus (before and one month after administration of ⅕ dose of the plain polysaccharide vaccine):

Determination of geometric mean titers and concentrations (GMTs and GMCs) with 95% confidence intervals (95% CI)

Determination of the percentage of subjects with antibody titer/concentration above the proposed cutoffs with exact 95% CI (seropositivity/seroprotection rates)

Investigation of antibody titers/concentration after vaccination using reverse cumulative curves Computation of standardized asymptotic 95% CI for the difference in seropositivity/seroprotection rate between the primed group (Groups K, L, M and N) and the unprimed group (Group O)

Determination of the geometric mean of individual ratio of SBA-MenC titer over anti-PSC concentration, with 95% CI Determination of the 95% CI for the post-vaccination GMT/C ratio between the groups K, L, M and the control group N for anti-PRP and anti-tetanus and between each primed group (Groups K, L, M and N) and the unprimed group (Group O) for SBA-MenC and anti-PSC using an ANOVA model Results

TABLE 1

SBA-MenC titres and anti-PSC antibody concentration after booster vaccination

| Antibody | Group | N | GMT/C | 95% CL LL | 95% CL UL |
|---|---|---|---|---|---|
| SBA-MenC | K - MenC-TT | 71 | 3508.9 | 2580.1 | 4772.2 |
| | L - HibMenC | 79 | 2530.1 | 1831.7 | 3494.7 |
| | M - HibMenC | 81 | 5385.4 | 4425.0 | 6554.2 |
| | N - Meningitec | 85 | 1552.6 | 1044.4 | 2307.9 |
| | O - Control | 91 | 9.3 | 6.3 | 13.6 |
| Anti-PSC | K - MenC-TT | 70 | 28.10 | 22.59 | 34.95 |
| | L - HibMenC | 71 | 30.01 | 24.09 | 37.38 |
| | M - HibMenC | 76 | 34.58 | 29.10 | 41.09 |
| | N - Meningitec | 78 | 16.59 | 12.98 | 21.21 |
| | O - Control | 94 | 3.05 | 2.36 | 3.93 |

Group K: subjects primed with MenC10-TT + Infanrix. hexa;
Group L: subjects primed with Hib10-MenC10-TT + Infanrix. penta;
Group M: subjects primed with Hib5-MenC5-TT + Infanrix. penta;
Group N: subjects primed with Meningitec. + Infanrix. hexa;
Group O: control subjects (i.e. subjects not primed with MenC conjugate vaccine)
N: number of subjects with available results Higher titres of antibodies against MenC and higher SBA titres were achieved by priming with the larger sized MenC polysaccharide conjugate vaccines (groups K, L and M) compared with the Meningitec oligosaccharide conjugate vaccine.

TABLE 2

Geometric mean ratio for SBA_MenC titre/anti-PSC concentration

| Group | Timing | N | GMR | LL | UL |
|---|---|---|---|---|---|
| K | Pre | 70 | 49.470 | 34.939 | 70.044 |
|   | Post | 66 | 126.138 | 101.419 | 156.882 |
| L | Pre | 76 | 36.528 | 25.849 | 51.621 |
|   | Post | 70 | 90.200 | 70.153 | 115.975 |
| M | Pre | 77 | 51.298 | 36.478 | 72.139 |
|   | Post | 74 | 164.950 | 139.304 | 195.318 |
| N | Pre | 84 | 22.571 | 16.521 | 30.837 |
|   | Post | 76 | 90.168 | 67.757 | 119.991 |
| O | Pre | 3 | 91.634 | 0.651 | 12889.8 |
|   | Post | 87 | 2.708 | 1.767 | 4.149 |

In all four primed groups (Groups K, L, M and N), the GMR increased significantly from pre to post booster vaccination indicating the presence of antibody maturation and functionality. GMR in the Group M (primed with Hib5-MenC5-TT) was higher than in the Group N (primed with Meningitec™)

TABLE 3

Persistence at 12-15 months of age just prior to administration of the booster vaccines

| Endpoints | Group | N | % | Group | N | % | Difference | Value % |
|---|---|---|---|---|---|---|---|---|
| SBAMenC ≥ 1:8 | K | 79 | 88.6 | N | 91 | 80.2 | N − K | −8.4 |
|  | L | 84 | 93.3 | N | 91 | 80.2 | N − L | −3.1 |
|  | M | 85 | 87.1 | N | 91 | 80.2 | N − M | −6.8 |
| SBAMenC ≥ 1:128 | K | 79 | 65.8 | N | 91 | 51.6 | N − K | −14.2 |
|  | L | 84 | 56.0 | N | 91 | 51.6 | N − L | −4.3 |
|  | M | 85 | 64.7 | N | 91 | 51.6 | N − M | −13.1 |
| Anti-PSC ≥ 0.3 μg/ml | K | 79 | 100.0 | N | 91 | 100.0 | N − K | 0.0 |
|  | L | 84 | 100.0 | N | 91 | 100.0 | N − L | 0.0 |
|  | M | 88 | 98.9 | N | 91 | 100.0 | N − M | 1.1 |
| Anti-PSC ≥ 2 μg/ml | K | 79 | 72.2 | N | 91 | 81.3 | N − K | 9.2 |
|  | L | 84 | 64.3 | N | 91 | 81.3 | N − L | 17.0 |
|  | M | 88 | 64.3 | N | 91 | 81.3 | N − M | 8.6 |
| Anti-PRP ≥ 0.15 μg/ml | K | 81 | 88.9 | N | 91 | 85.7 | N − K | −3.2 |
|  | L | 86 | 96.5 | N | 91 | 85.7 | N − L | −10.8 |
|  | M | 90 | 98.9 | N | 91 | 85.7 | N − M | −13.2 |
| Anti-PRP ≥ 1 μg/ml | K | 81 | 33.3 | N | 91 | 28.6 | N − K | −4.8 |
|  | L | 86 | 55.8 | N | 91 | 28.6 | N − L | −27.2 |
|  | M | 90 | 74.4 | N | 91 | 28.6 | N − M | −45.9 |
| Anti-tetanus ≥ 0.1 IU/ml | K | 81 | 100.0 | N | 91 | 96.7 | N − K | −3.3 |
|  | L | 86 | 100.0 | N | 91 | 96.7 | N − L | −3.3 |
|  | M | 90 | 100.0 | N | 91 | 96.7 | N − M | −3.3 |

Group K: subjects primed with MenC10-TT + Infanrix. hexa;
Group L: subjects primed with Hib10-MenC10-TT + Infanrix. penta;
Group M: subjects primed with Hib5-MenC5-TT + Infanrix. penta;
Group N: subjects primed with Meningitec. + Infanrix. hexa;
N: number of subjects with available results Higher SBA titres against MenC were achieved by priming with the larger size of MenC (groups K, L and M) compared to priming with the MenC-oligosaccharide conjugate Meningitec.

Immune Memory (ATP Cohort for Immunogenicity)

Administration of ⅕ dose of the plain polysaccharide ACWY vaccine elicited very high SBA-MenC titer in all four primed groups with 98.7-100% and 97.5-100% of subjects primed with a candidate vaccine regimen exhibiting titers ≥1:8 and ≥1:128, respectively. In the group primed with the Meningitec™ regimen, there was a trend for a lower percentage of subjects with titers ≥1:128 (91.8%). In comparison, 17.6% of unprimed subjects had SBA MenC titers ≥1:8 and ≥1:128.

Example 4

Phase II Clinical Trial on HibMenAC-TT Conjugate Vaccine Mixed with DTPw-HepB

Study Design:
Open, randomized (1:1:1:1:1), single centre study with five groups. The five groups received the following vaccination regimen respectively, at 6, 10 and 14 weeks of age.

Tritanrix.-HepB/Hib-MenAC 2.5 μg/2.5 μg/2.5 μg: henceforth referred to as 2.5/2.5/2.5

Tritanrix.-HepB/Hib-MenAC 2.5 μg/5 μg/5 μg: henceforth referred to as 2.5/5/5

Tritanrix.-HepB/Hib-MenAC 5 μg/5 μg/5 μg: henceforth referred to as 5/5/5

Tritanrix.-HepB+Hiberix.: henceforth referred to as Hiberix

Tritanrix.-HepB/Hiberix.+Meningitec.: henceforth referred to as Meningitec

Blood samples were taken at the time of the first vaccine dose (Pre) and one month after the third vaccine dose (Post-dose 3).

Tritanrix is a DTPw vaccine marketed by GlaxoSmithKline Biologicals S.A.

105 subjects were used in each of the five groups giving a total of 525 subjects in the study.

TABLE 4

Content of GSK vaccine formulations

| Components per dose (0.5 ml) | 2.5/2.5/2.5* | 2.5/5/5 | 5/5/5 |
|---|---|---|---|
| Hib capsular polysaccharide PRP conjugated to tetanus toxoid (TT) | 2.5 μg | 2.5 μg | 5 μg |
| *Neisseria meningitidis* A capsular polysaccharide (PSA) conjugated to TT | 2.5 μg | 5 μg | 5 μg |
| *Neisseria meningitidis* C capsular polysaccharide (PSC) conjugated to TT | 2.5 μg | 5 μg | 5 μg |

*The 2.5/2.5/2.5 vaccine was a dose dilution of GSK Biologicals' Hib-MenAC 5/5/5 vaccine containing 2.5 μg of each of PRP-TT, MenA-TT and MenC-TT.

The Hib-MenAC vaccine formulations were mixed extemporaneously with Tritanirx-HepB. GSK Biologicals' combined diphtheria-tetanus-whole cell *Bordetella pertussis*-hepatitis B (DTPw-HB) vaccine (Tritanrix-HepB) contains not less than 30 International Units (IU) of diphtheria toxoid, not less than 60 IU of tetanus toxoid, not less than 4 IU of killed *Bordetella pertussis* and 10 μg of recombinant hepatitis B surface antigen.

Reference Therapy, Dose, Mode of Administration, Lot No.:
Vaccination Schedule/Site:
One group received Tritanrix.-HepB vaccine intramuscularly in the left thigh and Hiberix™ intramuscularly in the right thigh at 6, 10 and 14 weeks of age. Another group received Tritanrix™-HepB/Hiberix™ vaccine intramuscularly in the left thigh and Meningitec vaccine intramuscularly in the right thigh at 6, 10 and 14 weeks of age.

Vaccine/Composition/Dose/Lot Number:
The Tritanrix™-HepB vaccine used was as described above.

One dose (0.5 ml) of GSK Biologicals' *Haemophilus influenzae* type b conjugate vaccine: Hiberix™ contained 10 μg of PRP conjugated to tetanus toxoid. In the Hiberix™ Group, it was mixed with sterile diluent and in the Meningitec™ Group it was mixed with Tritanrix™-HepB.

One dose (0.5 ml) of Wyeth Lederle's MENINGITEC™ vaccine contained: 10 μg of capsular oligosaccharide of meningococcal group C conjugated to 15 μg of *Corynebacterium diphtheria* CRM197 protein and aluminium as salts.

Results—Immune Responses Generated Against Hib, MenA and MenC

TABLE 5a

Anti - PRP (μg/ml)

| Group | 2.5/2.5/2.5 % 95% CL GMC/T LL UL | 2.5/5/5 % 95% CL GMC/T LL UL | 5/5/5 % 95% CL GMC/T LL UL | Hiberix ™ % 95% CL GMC/T LL UL | Meningitec ™ % 95% CL GMC/T LL UL |
|---|---|---|---|---|---|
| % ≥ 0.15 | 100 96.5 100 | 99.0 94.8 100 | 100 96.5 100 | 100 96.5 100 | 100 96.5 100 |
| GMC | 20.80 15.96 27.10 | 22.62 17.72 28.88 | 19.36 15.33 24.46 | 38.55 29.93 49.64 | 10.94 8.62 13.88 |

TABLE 5b

SBA - MenC

| Group | 2.5/2.5/2.5 % 95% CL GMC/T LL UL | 2.5/5/5 % 95% CL GMC/T LL UL | 5/5/5 % 95% CL GMC/T LL UL | Hiberix ™ % 95% CL GMC/T LL UL | Meningitec ™ % 95% CL GMC/T LL UL |
|---|---|---|---|---|---|
| % ≥ 1:8 | 99 94.7 100 | 100 96.5 100 | 100 96.5 100 | 2.9 0.6 8.4 | 100 96.5 100 |
| GMT | 3132 2497 3930 | 4206 3409 5189 | 3697 3118 4384 | 4.7 3.9 5.6 | 4501 3904 5180 |

TABLE 5c

SBA MenA

| Group | 2.5/2.5/2.5 % 95% CL GMC/T LL UL | 2.5/5/5 % 95% CL GMC/T LL UL | 5/5/5 % 95% CL GMC/T LL UL | Hiberix ™ % 95% CL GMC/T LL UL | Meningitec ™ % 95% CL GMC/T LL UL |
|---|---|---|---|---|---|
| % ≥ 1:8 | 99.7 91.9 99.7 | 100 95.8 100 | 100 96.2 100 | 6.8 2.5 14.3 | 9.1 4.0 17.1 |
| GMT | 316.7 251.4 398.9 | 418.5 358.6 488.5 | 363 310.5 424.4 | 5.6 4.3 7.4 | 5.6 4.4 7.2 |

TABLE 5d

Anti-PSC (μg/ml)

| Group | 2.5/2.5/2.5 % 95% CL GMC/T LL UL | 2.5/5/5 % 95% CL GMC/T LL UL | 5/5/5 % 95% CL GMC/T LL UL | Hiberix ™ % 95% CL GMC/T LL UL | Meningitec ™ % 95% CL GMC/T LL UL |
|---|---|---|---|---|---|
| % ≥ 0.3 | 100 96.5 100 | 100 96.4 100 | 100 96.5 100 | 8.2 3.6 15.6 | 100 96.5 100 |
| GMC | 49.03 43.24 55.59 | 71.11 62.49 80.92 | 61.62 54.88 69.20 | 0.17 0.15 0.19 | 58.02 51.42 65.46 |

TABLE 5e

| Group | 2.5/2.5/2.5 % 95% CL GMC/T LL UL | 2.5/5/5 % 95% CL GMC/T LL UL | 5/5/5 % 95% CL GMC/T LL UL | Hiberix ™ % 95% CL GMC/T LL UL | Meningitec ™ % 95% CL GMC/T LL UL |
|---|---|---|---|---|---|
| % ≥ 0.3 | 100 96.4 100 | 100 96.5 100 | 99.0 94.8 100 | 1.0 0.0 5.4 | 5.9 2.2 12.5 |
| GMC | 18.10 15.34 21.35 | 26.51 22.93 30.79 | 23.40 20.05 27.30 | 0.15 0.15 0.15 | 0.17 0.15 0.18 |

Conclusion

A comparison of the immunogenicity results achieved using the oligosaccharide MenC-CRM197 conjugate vaccine and the three GSK formulations which contain polysaccharide MenA-TT and MenC-TT conjugates showed that the polysaccharide Men conjugates were able to elicit a good immunogenic response similar to that achieved using the oligosaccharide conjugate vaccine Meningitec. All formulations tested gave a response to MenC in 100% of patients.

Example 5

\Phase II Clinical Trial Administering Hib MenCY Concomitantly with Infanrix Penta According to a 2, 3 and 4 Month Schedule Study Design:

A Phase II, open (partially double-blind*) randomized controlled multi-center study with 5 groups receiving a three-dose primary schedule with vaccines as follows:
  Group Hib-MenCY 2.5/5/5: Hib-MenCY (2.5/5/5)+Infanrix™ penta
  Group Hib-MenCY 5/10/10: Hib-MenCY (5/10/10)+Infanrix™ penta
  Group Hib-MenCY 5/5/5: Hib-MenCY (5/5/5)+Infanrix™ penta
  Group Hib-MenC: Hib-MenC (5/5)+Infanrix™ penta
  Group Menjugate: Menjugate™**+Infanrix™ hexa (control).
  *Hib-MenCY 2.5/5/5, Hib-MenCY 5/10/10 and Hib-MenC were administered in a double-blind manner while the Hib-MenCY 5/5/5 group and the Menjugate group were open. The 2.5/5/5, 5/10/10 and 5/5/5 formulations of Hib-MenCY contain MenC native polysaccharides and MenY polysaccharides which are microfluidized.
  **Menjugate™ contains 10 µg of MenC oligosaccharides conjugated to 12.5-25 µm of CRM197 per dose and is produced by Chiron.

Vaccination at +/−2, 3, 4 months of age (Study Month 0, Month 1 and Month 2), and blood samples (3.5 ml) from all subjects prior to and one month post primary vaccination (Study Month 0 and Month 3).

Study Vaccine, Dose, Mode of Administration, Lot Number:

Three doses injected intramuscularly at one month intervals, at approximately 2, 3 and 4 months of age as follows:

TABLE 6

Vaccines administered (study and control), group, schedule/site and dose

| Group | Schedule (months of age) | Vaccine dose administered Site-Left upper thigh | Concomitant vaccine administered Site Right upper thigh |
|---|---|---|---|
| Hib-MenCY 2.5/5/5 | 2, 3, and 4 | Hib (2.5 µg)-MenC-TT (5 µg)-MenY-TT (5 µg) | DTPa-HBV-IPV (Infanrix ™ penta) |
| Hib-MenCY 5/10/10 | 2, 3, and 4 | Hib (5 µg)-MenC-TT (10 µg)-MenY-TT (10 µg) | DTPa-HBV-IPV (Infanrix ™ penta) |
| Hib-MenCY 5/5/5 | 2, 3, and 4 | Hib (5 µg)-MenC-TT (5 µg)-MenY-TT (5 µg) | DTPa-HBV-IPV (Infanrix ™ penta) |
| Hib-MenC | 2, 3, and 4 | Hib (5 µg)-Men C (5 µg) | DTPa-HBV-IPV (Infanrix ™ penta) |
| Menjugate ™ | 2, 3, and 4 | Menjugate ™ | DTPa-HBV-IPV/Hib (Infanrix ™hexa) |

Immunogenicity:

Measurement of antibody titres/concentrations against each vaccine antigen:

Prior to the first dose (Month 0) and approximately one month after the third dose (Month 3) in all subjects for: SBA-MenC and SBA-MenY, anti-PSC and anti-PSY, anti-PRP, anti-T, anti-FHA, anti-PRN and anti-PT. Using serum bactericidal activity against N. meningitidis serogroups C and Y (SBA-MenC and SBA-MenY cut-off: 1:8 and 1:128); ELISA assays with cut-offs: ≥0.3 µg/ml and ≥2 µg/ml for anti-N. meningitidis serogroups C and Y polysaccharides (anti-PSC IgG and anti-PSY IgG); ≥0.15 µg/ml and ≥1.0 µg/ml for Hib polysaccharide polyribosil-ribitol-phosphate (anti-PRP IgG); 5EL.U/ml for anti-FHA, anti-PRN, anti-PT; ≥0.1 IU/ml anti-tetanus toxoid (anti-TT). Only at one month after the third dose (Month 3) in all subjects for: anti-D, anti-HBs and anti-polio 1, 2 and 3. Using ELISA assays with cut-offs: 0.1 IU/ml for anti-diphtheria (anti-D); ≥10 mIU/ml for antihepatitis B (anti-HBs); and microneutralization test cut-off: 1:8 for anti-polio type 1, 2 and 3 (anti-polio 1, 2 and 3).

Statistical Methods:

The seroprotection/seropositivity rates and geometric mean concentrations/titres (GMCs/GMTs) with 95% confidence intervals (95% CI) were computed per group, for SBA-MenC, anti-PSC, SBA-MenY, anti-PSY, anti-PRP, anti-Tetanus, anti-PT, anti-FHA and anti-PRN prior to and one month after vaccination; for anti-Diphtheria, anti-HBs, anti-Polio 1, anti-Polio 2 and anti-Polio 3 one month after vaccination. Vaccine response (appearance of antibodies in subjects initially seronegative or at least maintenance of antibody concentrations in subjects initially seropositive) with 95% CI for anti-PT, anti-PRN and anti-FHA were also computed one month after vaccination. Reverse cumulative curves for each antibody at Month 3 are also presented. The differences between the Hib-MenCY and the Hib-MenC groups, compared with the Menjugate™ control group were evaluated in an exploratory manner for each antibody, except for SBA-MenY and anti-PSY, in terms of (1) the difference between the Menjugate™ group (minus) the Hib-MenCY and Hib-MenC groups for the percentage of subjects above the specified cut-offs or with a vaccine response with their standardized asymptotic 95% CI, (2) the GMC or GMT ratios of the Menjugate™ group over the Hib-MenCY and Hib-MenC groups with their 95% CI. The same comparisons were done to evaluate the difference between each pair of Hib-MenCY formulations for anti-PRP, SBA-MenC, anti-PSC, SBA-MenY, anti-PSY and anti-TT antibodies.

Seroprotection/Seropositivity Rates & GMC/Ts (ATP Cohort for Immunogenicity)

TABLE 7a

Anti-PRP (n/ml)

| Group | N | % ≥ 0.15 | LL | UL | ≥1 | LL | UL | GMC | LL | UL |
|---|---|---|---|---|---|---|---|---|---|---|
| Hib MenCY 2.5/5/5 | 67 | 100.0 | 94.6 | 100.0 | 98.5 | 92.0 | 100.0 | 9.01 | 7.25 | 11.21 |
| Hib MenCY 5/10/10 | 67 | 100.0 | 94.6 | 100.0 | 98.5 | 92.0 | 100.0 | 9.49 | 7.72 | 11.65 |
| Hib MenCY 5/5/5 | 70 | 100.0 | 94.9 | 100.0 | 98.6 | 92.3 | 100.0 | 8.08 | 6.53 | 9.98 |
| Hib MenC | 74 | 100.0 | 95.1 | 100.0 | 98.6 | 92.7 | 100.0 | 10.44 | 8.49 | 12.83 |
| Menjugate™ | 71 | 100.0 | 94.9 | 100.0 | 80.3 | 69.1 | 88.8 | 2.60 | 1.97 | 3.43 |

TABLE 7b

SBA-MenC (Titre)

| Group | N | % ≥ 1:8 | LL | UL | ≥1:128 | LL | UL | GMT | LL | UL |
|---|---|---|---|---|---|---|---|---|---|---|
| Hib MenCY 2.5/5/5 | 70 | 100.0 | 94.9 | 100.0 | 95.7 | 88.0 | 99.1 | 1005.8 | 773.5 | 1308.0 |
| Hib MenCY 5/10/10 | 67 | 100.0 | 94.6 | 100.0 | 94.0 | 85.4 | 98.3 | 1029.8 | 799.7 | 1326.0 |
| Hib MenCY 5/5/5 | 71 | 100.0 | 94.9 | 100.0 | 94.4 | 86.2 | 98.4 | 906.9 | 691.3 | 1189.8 |
| Hib MenC | 74 | 100.0 | 95.1 | 100.0 | 95.9 | 88.6 | 99.2 | 871.0 | 677.3 | 1120.0 |
| Menjugate™ | 71 | 100.0 | 94.9 | 100.0 | 100.0 | 94.9 | 100.0 | 3557.6 | 2978.8 | 4248.8 |

TABLE 7c

Anti-PSC (µg/ml)

| Group | N | % ≥ 0.3 | LL | UL | ≥2 | LL | UL | GMC | LL | UL |
|---|---|---|---|---|---|---|---|---|---|---|
| Hib MenCY 2.5/5/5 | 69 | 100.0 | 94.8 | 100.0 | 100.0 | 94.8 | 100.0 | 21.70 | 18.36 | 25.65 |
| Hib MenCY 5/10/10 | 66 | 100.0 | 94.6 | 100.0 | 100.0 | 94.6 | 100.0 | 27.26 | 23.26 | 31.95 |
| Hib MenCY 5/5/5 | 70 | 100.0 | 94.9 | 100.0 | 100.0 | 94.9 | 100.0 | 19.02 | 16.49 | 21.93 |

TABLE 7c-continued

| | Anti-PSC (μg/ml) | | | | | | | | |
|---|---|---|---|---|---|---|---|---|---|
| Group | N | % ≥ 0.3 | LL | UL | ≥2 | LL | UL | GMC | LL | UL |
| Hib MenC | 74 | 100.0 | 95.1 | 100.0 | 100.0 | 95.1 | 100.0 | 21.08 | 18.24 | 24.35 |
| Menjugate ™ | 71 | 100.0 | 94.9 | 100.0 | 100.0 | 94.9 | 100.0 | 38.49 | 33.64 | 44.05 |

TABLE 7d

| | SBA-MenY (Titre) | | | | | | | | |
|---|---|---|---|---|---|---|---|---|---|
| Group | N | % ≥ 1:8 | LL | UL | ≥1:128 | LL | UL | GMT | LL | UL |
| Hib MenCY 2.5/5/5 | 69 | 97.1 | 89.9 | 99.6 | 92.8 | 83.9 | 97.6 | 470.7 | 351.1 | 631.2 |
| Hib MenCY 5/10/10 | 66 | 97.0 | 89.5 | 99.6 | 86.4 | 75.7 | 93.6 | 437.1 | 322.0 | 593.4.8 |
| Hib MenCY 5/5/5 | 71 | 98.6 | 92.4 | 100.0 | 95.8 | 88.1 | 99.1 | 635.3 | 501.5 | 804.8 |
| Hib MenC | 74 | 21.6 | 12.9 | 32.7 | 13.5 | 6.7 | 23.5 | 9.3 | 6.3 | 13.7 |
| Menjugate ™ | 71 | 19.7 | 11.2 | 30.9 | 9.9 | 4.1 | 19.3 | 7.5 | 5.4 | 10.4 |

TABLE 7e

| | Anti-PSY (μg/ml) | | | | | | | | |
|---|---|---|---|---|---|---|---|---|---|
| Group | N | % ≥ 0.3 | LL | UL | ≥2 | LL | UL | GMC | LL | UL |
| Hib MenCY 2.5/5/5 | 69 | 100.0 | 94.8 | 100.0 | 100.0 | 94.8 | 100.0 | 26.86 | 22.86 | 31.56 |
| Hib MenCY 5/10/10 | 66 | 100.0 | 94.6 | 100.0 | 100.0 | 94.6 | 100.0 | 37.02 | 31.84 | 43.04 |
| Hib MenCY 5/5/5 | 70 | 100.0 | 94.9 | 100.0 | 100.0 | 94.9 | 100.0 | 23.57 | 19.94 | 27.86 |
| Hib MenC | 74 | 8.1 | 3.0 | 16.8 | 4.1 | 0.8 | 11.4 | 0.19 | 0.15 | 0.25 |
| Menjugate ™ | 71 | 5.6 | 1.6 | 13.8 | 1.4 | 0.0 | 7.6 | 0.17 | 0.15 | 0.19 |

TABLE 7f

| | Anti-tetanus (IU/ml) | | | | | |
|---|---|---|---|---|---|---|
| Group | N | % ≥ 0.1 | LL | UL | GMC | LL | UL |
| Hib MenCY 2.5/5/5 | 68 | 100.0 | 94.7 | 100.0 | 3.06 | 2.63 | 3.55 |
| Hib MenCY 5/10/10 | 67 | 100.0 | 94.6 | 100.0 | 3.25 | 2.88 | 3.68 |
| Hib MenCY 5/5/5 | 70 | 100.0 | 94.9 | 100.0 | 2.97 | 2.59 | 3.41 |
| Hib MenC | 74 | 100.0 | 95.1 | 100.0 | 3.15 | 2.73 | 3.64 |
| Menjugate ™ | 71 | 100.0 | 94.9 | 100.0 | 1.66 | 1.39 | 1.97 |

Group Hib-MenCY 2.5/5/5: Hib-MenCY (2.5/5/5)+Infanrix™ penta

Group Hib-MenCY 5/10/10: Hib-MenCY (5/10/10)+Infanrix™ penta

Group Hib-MenCY 5/5/5: Hib-MenCY (5/5/5)+Infanrix™ penta

Group Hib-MenC: Hib-Men (5/5)+Infanrix™ hexa

Group Menjugate: Menjugate™+Infanrix™ penta

N=number of subjects with available results. %=percentage of subjects with concentration/titre within the specified range GMC/T: geometric mean concentration/titre 95% CI=95% confidence interval; LL=Lower Limit; UL=Upper Limit Conclusion The MenC and Y polysaccharide conjugates produced a good immune response in all subjects with 100% of subjects producing above 0.3 μg/ml responses against MenC and MenY.

Example 6

Phase II Clinical Trial Comparing Three Formulations of MenACWY-TT with Meningitec MenC-CRM197 Oligosaccharide-Conjugate Vaccine This example reports a phase II, open (partially-blind), randomized, controlled dose-range study to evaluate the Immunogenicity of three different formulations of GlaxoSmithKline Biological's meningococcal serogroups A, C, W-135, Y tetanus toxoid conjugate (MenACWY-TT) vaccine in comparison to a MenC oligosaccharide-CRM197 conjugate vaccine (Meningitec) when given as one dose to children aged 12-14 months.

The clinical trial was an open (partially double-blind*), controlled, multicentric study in which eligible subjects of 12-14 months were randomized (1:1:1:1) to one of four parallel groups of 50 subjects to receive a single primary dose at Visit 1 as follows:

Form 1T: MenACWY-TT at a dose of 2.5 μg of MenA polysaccharide conjugated to tetanus toxoid (TT), 2.5 μg of MenC polysaccharide conjugated to TT, 2.5 μg of MenW polysaccharide conjugated to TT and 2.5 μg of MenY polysaccharide conjugated to TT.

Form 2T: MenACWY-TT at a dose of 5 μg of MenA polysaccharide conjugated to TT, 5 μg of MenC polysaccharide conjugated to TT, 5 μg of MenW polysaccharide conjugated to TT and 5 μg of MenY polysaccharide conjugated to TT.

Form 3T: MenACWY-TT at a dose of 2.5 μg of MenA polysaccharide conjugated to TT, 10 μg of MenC polysaccharide conjugated to TT, 2.5 μg of MenW polysaccharide conjugated to TT and 2.5 μg of MenY polysaccharide conjugated to TT.

Ctrl T: 10 μg MenC oligosaccharide conjugated to 12.5-25 μg CRM197 (Meningitec™).

*The three different MenACWY-TT formulations were administered in a double-blind manner.

Vaccination Schedule/Site:

A single vaccine dose was administered intramuscularly in the left deltoid at Visit 1 (Study Month 0) according to randomized assignment. All candidate vaccines were supplied as a lyophilized pellet in a monodose vial (0.5 ml after reconstitution with the supplied saline diluent).

Immunogenicity:

Measurement of titers/concentrations of antibodies against meningococcal vaccine antigen components in blood samples obtained prior to the study vaccine dose (Month 0) and approximately one month after the study vaccine dose (Month 1) in all subjects. Determination of bactericidal antibody titers against *N. meningitidis* serogroups A, C, W-135 and Y (SBA-MenA, SBA-MenC, SBA-MenW and SBA-MenY) by a bactericidal test (assay cut-offs: a dilution of 1:8 and 1:128) and ELISA measurement of antibodies against *N. meningitidis* serogroups A, C, W-135 and Y (anti-PSA, anti-PSC, anti-PSW and anti-PSY, assay cut-offs≥0.3 μg/ml and ≥2 μg/ml), and tetanus toxoid (anti-tetanus, assay cut-off 0.1 IU/ml).

Results

Antibody response in terms of the percentage of SBA-MenA, SBA-MenC, SBA-MenW and SBA-MenY responders one month after vaccination (the primary endpoint) is shown in Table 8. A response is defined as greater than or equal to a 4-fold increase for seropositive subjects or seroconversion for seronegative subjects before vaccination.

TABLE 8

Vaccine responses for SBA antibody one month after vaccination

| Antibody | Group | N | % | LL | UL |
|---|---|---|---|---|---|
| SBA-MenA | Form 1T | 42 | 61.9 | 45.6 | 76.4 |
| | Form 2T | 39 | 82.1 | 66.5 | 92.5 |
| | Form 3T | 40 | 62.5 | 45.8 | 77.3 |
| | Meningitec ™ | 36 | 11.1 | 3.1 | 26.1 |
| SBA-MenC | Form 1T | 46 | 97.8 | 88.5 | 99.9 |
| | Form 2T | 43 | 100.0 | 91.8 | 100.0 |
| | Form 3T | 44 | 95.5 | 84.5 | 99.4 |
| | Meningitec ™ | 49 | 91.8 | 80.4 | 97.7 |
| SBA-MenW | Form 1T | 45 | 100.0 | 92.1 | 100.0 |
| | Form 2T | 43 | 97.7 | 87.7 | 99.9 |
| | Form 3T | 45 | 100.0 | 92.1 | 100.0 |
| | Meningitec ™ | 46 | 15.2 | 6.3 | 28.9 |
| SBA-MenY | Form 1T | 47 | 97.9 | 88.7 | 99.9 |
| | Form 2T | 44 | 88.6 | 75.4 | 96.2 |
| | Form 3T | 45 | 93.3 | 81.7 | 98.6 |
| | Meningitec ™ | 49 | 4.1 | 0.5 | 14.0 |

Table 9 shows the numbers of subjects achieving SBA titres over cutoff points of 1:8 and 1:128 as well as GMTs.

TABLE 9

Seropositivity rates and GMTs for SBA antibodies one month after vaccination

| | Group | N | % | ≥1:8 LL | UL | % | ≥1:128 LL | UL | GMT |
|---|---|---|---|---|---|---|---|---|---|
| SBA-MenA | Form 1T | 46 | 100 | 92.3 | 100 | 100 | 92.3 | 100 | 1457.3 |
| | Form 2T | 45 | 100 | 92.1 | 100 | 97.8 | 88.2 | 99.9 | 1776.9 |
| | Form 3T | 48 | 97.9 | 88.9 | 99.9 | 97.9 | 88.9 | 99.9 | 1339.5 |
| | Meningitec ™ | 41 | 51.2 | 35.1 | 67.1 | 43.9 | 28.5 | 60.3 | 42.8 |
| SBA-MenC | Form 1T | 47 | 97.9 | 88.7 | 99.9 | 78.7 | 64.3 | 89.3 | 281.3 |
| | Form 2T | 45 | 100 | 92.1 | 100 | 84.4 | 70.5 | 93.5 | 428.6 |
| | Form 3T | 47 | 95.7 | 85.5 | 99.5 | 85.1 | 71.7 | 93.8 | 478.4 |
| | Meningitec ™ | 50 | 94.0 | 83.5 | 98.7 | 62.0 | 47.2 | 75.3 | 200.1 |
| SBA-MenW | Form 1T | 47 | 100 | 92.5 | 100 | 100 | 92.5 | 100 | 2529.1 |
| | Form 2T | 45 | 100 | 92.1 | 100 | 100 | 92.1 | 100 | 2501.6 |
| | Form 3T | 48 | 100 | 92.6 | 100 | 97.9 | 88.9 | 99.9 | 2300.2 |
| | Meningitec ™ | 48 | 27.1 | 15.3 | 41.8 | 6.3 | 1.3 | 17.2 | 9.4 |
| SBA-MenY | Form 1T | 47 | 100 | 92.5 | 100 | 100 | 92.5 | 100 | 1987.4 |
| | Form 2T | 45 | 100 | 92.1 | 100 | 100 | 92.1 | 100 | 2464.8 |
| | Form 3T | 48 | 100 | 92.6 | 100 | 97.9 | 88.9 | 99.9 | 2033.7 |
| | Meningitec ™ | 49 | 49.0 | 34.4 | 63.7 | 28.6 | 16.6 | 43.3 | 25.0 |

Vaccination with all three formulations of the ACWY-TT polysaccharide conjugate led to good SBA responses against MenA, MenC, MenW and MenY with 95-100% of subjects with titres greater than 1:8. In particular, the 5/5/5/5 and 2.5/10/2.5/2.5 formulations of the polysaccharide conjugates produced a higher response against MenC than the oligosaccharide Meningitic vaccine as seen by a higher proportion of subjects having a titre greater than 1:128 and the GMT readings.

Results

The results FIGS. 1A-1B show a trend towards higher immunogenicity for conjugates prepared using sized PSY. FIG. 1A shows the GMC results obtained in an ELISA for antisera raised against conjugates prepared from native MenY (ENYTT012), microfluidised MenY—40 cycles (ENYTT014) and microfluidised MenY—20 cycles (ENYTT015 bis). Higher GMCs were obtained where the MenY-TT was prepared from microfluidised MenY.

TABLE 10

Seropositivity rates and GMCs for anti polysaccharide antibodies one month after vaccination

|  | Group | N | ≥0.3 µg/ml % | LL | UL | ≥2 µg/ml % | LL | UL | GMC µg/ml |
|---|---|---|---|---|---|---|---|---|---|
| Anti-MenA | Form 1T | 47 | 93.6 | 82.5 | 98.7 | 68.1 | 52.9 | 80.9 | 2.35 |
|  | Form2T | 45 | 100 | 92.1 | 100 | 64.4 | 48.8 | 78.1 | 3.11 |
|  | Form3T | 48 | 95.8 | 85.7 | 99.5 | 37.5 | 24.0 | 52.6 | 1.65 |
|  | Meningitec ™ | 50 | 10.0 | 3.3 | 21.8 | 2.0 | 0.1 | 10.6 | 0.18 |
| Anti-MenC | Form 1T | 47 | 100 | 92.5 | 100 | 100 | 92.5 | 100 | 9.57 |
|  | Form2T | 45 | 100 | 92.1 | 100 | 100 | 92.1 | 100 | 12.53 |
|  | Form3T | 47 | 100 | 92.5 | 100 | 97.9 | 88.7 | 99.9 | 19.29 |
|  | Meningitec ™ | 49 | 98.0 | 89.1 | 99.9 | 93.9 | 83.1 | 98.7 | 7.95 |
| Anti-MenW | Form 1T | 47 | 100 | 92.5 | 100 | 80.9 | 66.7 | 90.9 | 4.56 |
|  | Form2T | 45 | 100 | 92.1 | 100 | 93.3 | 81.7 | 98.6 | 6.83 |
|  | Form3T | 48 | 93.8 | 82.8 | 98.7 | 72.9 | 58.2 | 84.7 | 2.88 |
|  | Meningitec ™ | 50 | 0.0 | 0.0 | 7.1 | 0.0 | 0.0 | 7.1 | 0.15 |
| Anti-MenY | Form 1T | 47 | 100 | 92.5 | 100 | 97.9 | 88.7 | 99.9 | 8.90 |
|  | Form2T | 45 | 100 | 92.1 | 100 | 100 | 92.1 | 100 | 12.78 |
|  | Form3T | 47 | 97.9 | 88.7 | 99.9 | 87.2 | 74.3 | 95.2 | 5.67 |
|  | Meningitec ™ | 50 | 2.0 | 0.1 | 10.6 | 0.0 | 0.0 | 7.1 | 0.15 |

All three formulations of the ACWY-TT polysaccharide conjugate vaccine produced good immune responses against MenA, MenC, MenW and MenY with between 93% and 100% of subjects achieving titres grater than 0.3 µg/ml. Higher GMC readings were achieved using the 5/5/5/5 and 2/5/10/2.5/2.5 formulations of the ACWY-TT polysaccharide conjugate vaccine in comparison with Meningitec™.

Example 7

Comparison of Immunogenicity of Native and Sized MenY Polysaccharide Conjugates

Mice (female DBA/2 of 6-8 wk) received two injections, 2 weeks apart, of PSY-TT by the subcutaneous route. Blood samples were taken 14 days after the second injection in order to perform anti-PSY ELISA and SBA using 51975 menY strain. Per injection, mice received 1 µg of PSY-TT (lyo non-ads formulation).

The conjugates described in table 11 were used.

TABLE 11

| Conjugates | ENYTT012 | ENYTT014 | ENYTT015 bis |
|---|---|---|---|
| PSY microfluidisation | NO | Yes (40 cycles) | Yes (20 cycles) |
| TT/PS ratio | 1/1 | 1/1 | 1/1 |

Similar results were obtained when the antisera were assessed by SBA assay (FIG. 1B). Again the higher GMT values were achieved using conjugates prepared from microfluidised MenY.

The invention claimed is:

1. A method of immunizing a human host against disease caused by *Neisseria meningitidis* infection, comprising administering to the host an immunoprotective dose of an immunogenic composition comprising: a stabilizing agent; and lyophilized *N. meningitidis* capsular polysaccharides from serogroups A, C, W, and Y, wherein:
   the serogroup A capsular polysaccharide has an average size of 300 kDa;
   the serogroup C capsular polysaccharide has an average size of 200 kDa;
   the serogroup Y capsular polysaccharide has an average size of 101-300 kDa;
   the serogroup W capsular polysaccharide has an average size of 101-300 kDa; and
   wherein each *N. meningitidis* capsular polysaccharide is a *N. meningitidis* capsular polysaccharide conjugate comprising a *N. meningitidis* capsular polysaccharide conjugated to a tetanus toxoid carrier protein,
   wherein the immunogenic composition elicits in the host an immune response which comprises an antibody titer against MenA, MenC, MenW, and Men Y greater than 0.3 µg/ml.

2. The method of claim 1, wherein the serogroup Y capsular polysaccharide has an average size of 190-300 kDa; and the serogroup W capsular polysaccharide has an average size of 190-300 kDa.

3. The method of claim 1, wherein the stabilizing agent comprises sucrose.

4. The method of claim 1, wherein the stabilizing agent comprises trehalose.

5. The method of claim 1, wherein the human is aged up to 14 months.

\* \* \* \* \*